US010690572B2

(12) United States Patent
Sangha

(10) Patent No.: US 10,690,572 B2
(45) Date of Patent: Jun. 23, 2020

(54) DIRECT SPECIMEN COLLECTION DEVICE AND CASSETTE

(71) Applicant: Laboratory Corporation of America Holdings, Burlington, NC (US)

(72) Inventor: Jangbir Sangha, Overland Park, KS (US)

(73) Assignee: LABORATORY CORPORATION OF AMERICA HOLDINGS, Burlington, NC (US)

( * ) Notice: Subject to any disclaimer, the term of this patent is extended or adjusted under 35 U.S.C. 154(b) by 361 days.

(21) Appl. No.: 15/431,590

(22) Filed: Feb. 13, 2017

(65) Prior Publication Data

US 2017/0234778 A1 Aug. 17, 2017

Related U.S. Application Data

(60) Provisional application No. 62/294,780, filed on Feb. 12, 2016, provisional application No. 62/452,737, filed on Jan. 31, 2017.

(51) Int. Cl.
| | | |
|---|---|---|
| *G01N 1/31* | (2006.01) | |
| *G01N 1/02* | (2006.01) | |
| *B01L 3/00* | (2006.01) | |
| *A61B 10/00* | (2006.01) | |
| *G01N 1/00* | (2006.01) | |

(52) U.S. Cl.
CPC ............ *G01N 1/31* (2013.01); *A61B 10/0051* (2013.01); *B01L 3/5029* (2013.01); *G01N 1/02* (2013.01); *B01L 2200/0678* (2013.01); *B01L 2300/021* (2013.01); *B01L 2300/04* (2013.01); *G01N 2001/007* (2013.01); *G01N 2001/022* (2013.01); *G01N 2001/028* (2013.01)

(58) Field of Classification Search
CPC ...... G01N 1/31; G01N 1/02; G01N 2001/028; G01N 2001/022; G01N 2001/007; B01L 3/5029; B01L 2200/0678; B01L 2300/021; B01L 2300/04
See application file for complete search history.

(56) References Cited

U.S. PATENT DOCUMENTS

| | | | | |
|---|---|---|---|---|
| 2003/0045814 | A1* | 3/2003 | Sangha | ............... A61B 10/0051 600/573 |
| 2005/0220677 | A1* | 10/2005 | Sangha | ................... A61B 90/96 422/550 |

* cited by examiner

*Primary Examiner* — Dennis White
(74) *Attorney, Agent, or Firm* — Robin L. Teskin; Baker, Donelson, Bearman, Caldwell & Berkowitz, PC

(57) ABSTRACT

The present disclosure relates to a specimen collection device comprising ventilation means for drying a collected specimen. The device further comprises a cassette into which the specimen collected is secured to maintain evidentiary chain of custody requirements while providing unobstructed access to a collected specimen for automated analysis. Methods of using the device are also provided.

13 Claims, 20 Drawing Sheets

DIRECT SPECIMEN COLLECTION DEVICE AND CASSETTE

CROSS-REFERENCE TO RELATED APPLICATIONS

This application claims the benefit of U.S. Provisional Patent Application No. 62/294,780 filed Feb. 12, 2016 and U.S. Provisional Patent Application No. 62/452,737 filed Jan. 31, 2017 the entire disclosures of which are incorporated herein by reference.

FIELD OF THE INVENTION

The present disclosure relates to a specimen collection device comprising ventilation means for efficiently drying a collected specimen and a cassette into which the specimen collected is secured to maintain evidentiary chain of custody requirements while providing unobstructed access to a collected specimen for automated analysis. Methods of using the device are also provided.

BACKGROUND OF THE INVENTION

Increasingly in law enforcement it is necessary to collect biological samples as evidence of a crime or for use as identifying information of a particular human as is the case of DNA collection from suspects. In the collection of biological specimens, it is necessary to associate information about the subject with the specimen at the time of collection, as there is no manner for identifying a biological specimen by simple inspection. Therefore, a useful form of evidence collection device for use with biological specimens will contain, at least, a suspect information portion for recording subject information data thereon.

The use of biological specimens as evidence further requires that the biological specimen be securely associated with the identifying information so as to assure that after collection of the specimen, the collection paper or absorbent cannot be intentionally or inadvertently switched to a different collection paper. At a minimum, a proper evidence collection device or holder should easily and clearly show that tampering was attempted either by damage to delicate indicia on the device or by overt damage to a strongly secured device. It is further beneficial if the evidence collection device can accommodate additional forms of evidence such as the application and storage of finger prints on the evidence holder.

A particular issue in the collection of the biological sample is that the sample collection is often taken from a living, uncooperative person. Often the sample is to be taken from the mouth of the suspect where a saliva or DNA specimen is needed. In this instance, the collection absorbent used will be attached to a handle or a stick. Once the specimen is on the absorbent, the handle is no longer needed, and presents a complicating factor in specimen storage and analysis due to the extra bulk and size of a handle.

The foregoing issues relate, generally, to a process referred to as evidence "chain of custody." "Chain of custody" encompasses the procedures and documentation used to maintain and demonstrate the chronological history of the evidence. Documentation should include, for example, name or initials of the individual collecting the evidence, each person or entity subsequently having custody of it, dates the items were collected or transferred, agency and case number, victim's or suspect's name, and a brief description of the item. In biological samples, the principles of evidence or sample identification involved in maintaining proper "chain of custody" are especially critical as a fluid or cellular biological sample, once collected onto an absorbent, presents no distinguishing characteristics. This lack of visual characteristics foils any attempt to properly identify such a biological fluid or cellular sample once it has become separated from its identifying information.

Another problem or issue presented in the analysis of biological specimens is the need to extract or transfer the collected sample from the original collection absorbent and onto an alternate medium to permit analysis or testing of the specimen using the analysis equipment that is available in the selected laboratory. Often it is necessary to separate the collection absorbent from its originally obtained identifying information that is directly associated with the original collection absorbent. This separation of specimen from identifying information can lead to mistakes in associating the specimen with the correct subject or suspect or can lead to the "chain of custody" being open to question in court and a failure of proof of a crime. Sample misidentification is a major source of error both in laboratory analysis and in substantiating criminal evidence.

Importantly, another issue relating to the collection of biological specimens is that biological specimens degrade, hindering or affecting downstream analysis. This is especially true if the collected biological specimen remains wet for extended periods of time, and/or is not treated with stabilizing formulations. Methods of stabilizing biological specimens used in the forensics community have streamlined the collection and extraction of biomolecules from a variety of samples. These methods include transferring a collected specimen from the collection swab to a stabilizing matrix that harbors storage medium, such as chaotropic salts, that slow down the degradation process. However, such stabilizing methods known in the art are associated with problems. In particular, the collected specimen may not transfer to the stabilizing matrix in a consistent or reproducible manner. Further, if the swab used to collect the sample is separate and distinct from the stabilizing matrix receiving the sample, then forensic chain of custody issues arise.

Accordingly, a need still exists for a specimen collection device that is securely associated with the specimen collection absorbent and subject identifying information, while providing ease of use for the collecting user in the field, efficient drying and preservation of the collected specimen, ease of storage, and compatibility with automated analysis equipment. Further, it would be beneficial if such device was tamper proof or tamper evident.

SUMMARY OF THE INVENTION

In one aspect, a specimen collection device comprising ventilation means for drying a collected specimen is provided. The device comprises a specimen collection assembly comprising a sample collection carrier and a collection absorbent connected to the specimen collection carrier through a raised cap, and a handle cover comprising an attachment means for removably connecting the handle to the specimen collection assembly. The handle cover permits manipulation of the specimen collection assembly during specimen collection when the handle cover is attached to the specimen collection assembly. The specimen collection device further comprises a sliding cover having an elongated body and a head connected to the body on one end of the body, wherein the sliding cover is removably and slidably connected to the handle cover. The sliding cover further comprises a protrusion that engages the raised cap when the sliding cover is moved forwardly on the handle cover thereby raising the head of the sliding cover above the collection absorbent and creating a ventilation gap between the sliding cover and the collection absorbent. The specimen collection device further comprises a specimen collector cassette into which the specimen collected is secured. The cassette has a registration track configured to register with the shape of the specimen collection assembly upon insertion of the specimen collection assembly into the registration track. The specimen collector cassette further comprises a void in unobstructed registration with the collection absorbent when the specimen collector assembly is attached to the specimen collector cassette, thereby providing unobstructed access to a collected specimen for automated analysis.

The specimen collection assembly may further comprise a cover and a means for attaching the cover to the specimen collection cassette, wherein the cover permits a user to press the cover into contact with the collection absorbent without the user directly contacting the collection absorbent. The specimen collection cassette may further comprise identification indicia and a clean punch area. The handle cover and the sliding cover may further comprise ventilation holes.

In another aspect, a specimen collection device comprising ventilation means for drying a collected specimen is provided. The device comprises a specimen collection assembly comprising a sample collection carrier and a collection absorbent connected to the specimen collection carrier through a raised cap, and a handle cover comprising an attachment means for removably connecting the handle to the specimen collection assembly. The handle cover further comprises ventilation holes. The handle cover permits manipulation of the specimen collection assembly during specimen collection when the handle cover is attached to the specimen collection assembly. The specimen collection device further comprises a sliding cover having an elongated body and a head connected to the body on one end of the body, wherein the sliding cover is removably and slidably connected to the handle cover. The sliding cover further comprises a protrusion that engages the raised cap when the sliding cover is moved forwardly on the handle cover thereby raising the head of the sliding cover above the collection absorbent and creating a ventilation gap between the sliding cover and the collection absorbent. The sliding cover further comprises ventilation holes. The specimen collection device further comprises a specimen collector cassette into which the specimen collected is secured. The cassette has a clean punch area and a registration track configured to register with the shape of the specimen collection assembly upon insertion of the specimen collection assembly into the registration track. The specimen collector cassette further comprises a void in unobstructed registration with the collection absorbent when the specimen collector assembly is attached to the specimen collector cassette, thereby providing unobstructed access to a collected specimen for automated analysis.

The specimen collection assembly may further comprise a cover and a means for attaching the cover to the specimen collection cassette, wherein the cover permits a user to press the cover into contact with the collection absorbent without the user directly contacting the collection absorbent. The specimen collection cassette may further comprise identification indicia.

In yet another aspect, a method of supporting a biological sample collection absorbent is provided. The method provides for collecting a biological specimen, efficiently drying the collected specimen, using the original absorbent in an automated analytical system, and allowing for storage of the biological sample collection absorbent. The method comprises providing a specimen collection assembly comprising a sample collection carrier and a collection absorbent connected to the specimen collection carrier through a raised cap. The method further comprises providing a handle cover comprising an attachment means for removably connecting the handle to the specimen collection assembly, wherein the handle cover permits manipulation of the specimen collection assembly during specimen collection when the handle cover is attached to the specimen collection assembly, and wherein the handle cover comprises ventilation holes. The method also comprises providing a sliding cover removably and slidably connected to the handle cover, the sliding cover having an elongated body and a head connected to the body on one end of the body and a protrusion that engages the raised cap when the sliding cover is moved forwardly on the handle cover thereby raising the head of the sliding cover above the collection absorbent and creating a ventilation gap between the head of the sliding cover and the collection absorbent, and wherein the head further comprises ventilation holes. In the method, the sample collection assembly and the sliding cover are connected to the handle cover to produce a sample collector. The sliding cover is slid backwardly to expose the sample collection absorbent to collect a specimen. A biological sample is collected by contacting the biological sample with the collection absorbent. After collecting the biological sample, the sliding cover is moved forwardly to cover the sample collection absorbent, thereby creating a ventilation gap between the handle cover and the collection absorbent. The sample is then allowed to dry. The sliding cover is then removed from the handle cover, the sample carrier is connected to a cassette, and the handle cover is removed from the sample collection carrier. The collection cassette is then stored.

The method may further comprise applying a preservative additive to the collection absorbent after collecting the biological sample, inserting the collection cassette into an automatic sampling device.

BRIEF DESCRIPTION OF THE DRAWINGS

The following drawings form part of the present disclosure and are included to further demonstrate certain aspects of the present disclosure. The disclosure may be better understood by reference to one or more of these drawings in combination with the detailed description of specific aspects presented herein.

DETAILED DESCRIPTION

Figure 1:
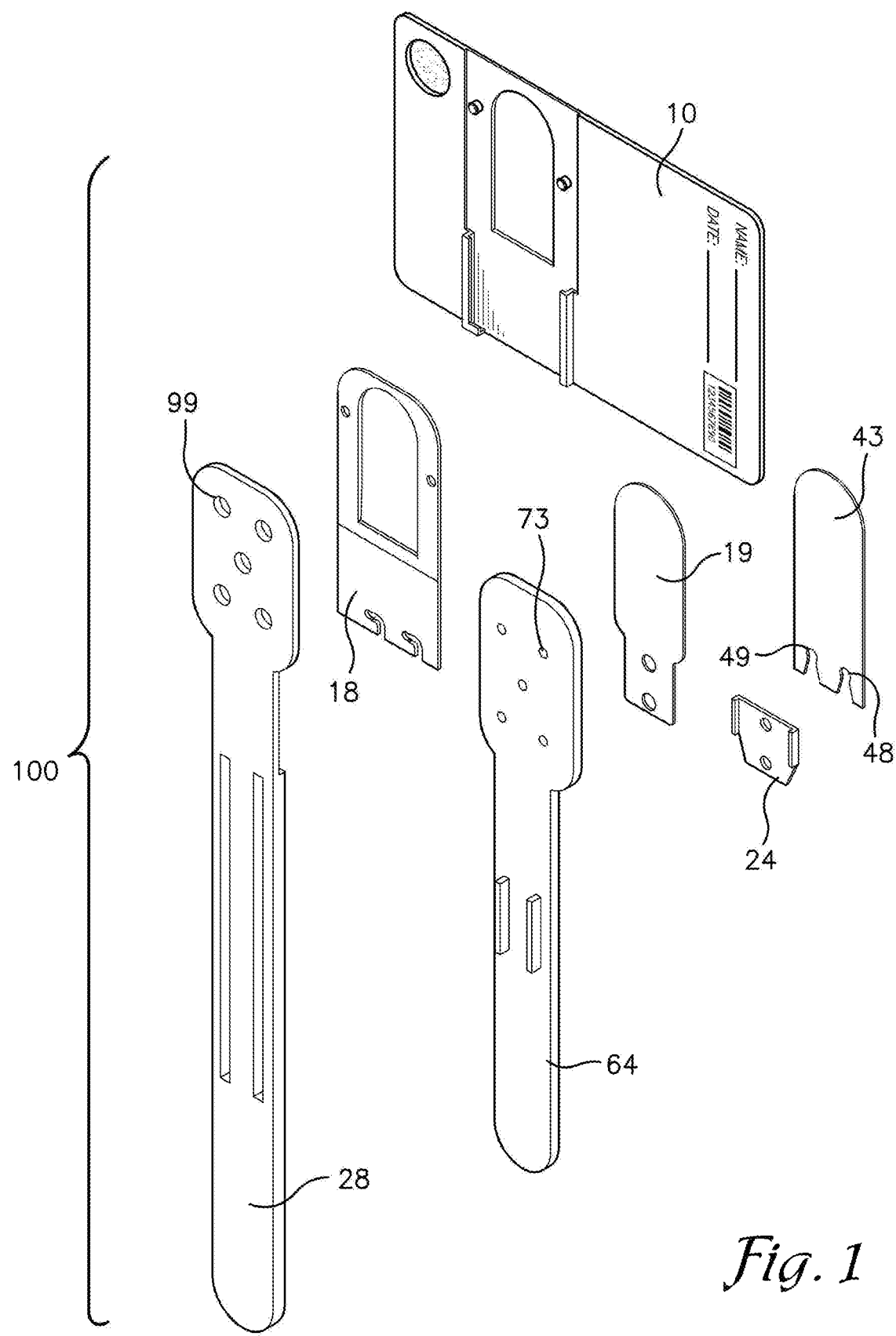
FIG. 1 is an exploded view of the specimen collection device 100 showing the cassette 10, the sample collection carrier 18, the collection absorbent 19, support cap 24, slider 64, the cover 43 with ventilation holes 73 and attachment means 48 and 49, and handle cover 28 with ventilation holes 99.
Figure 2:
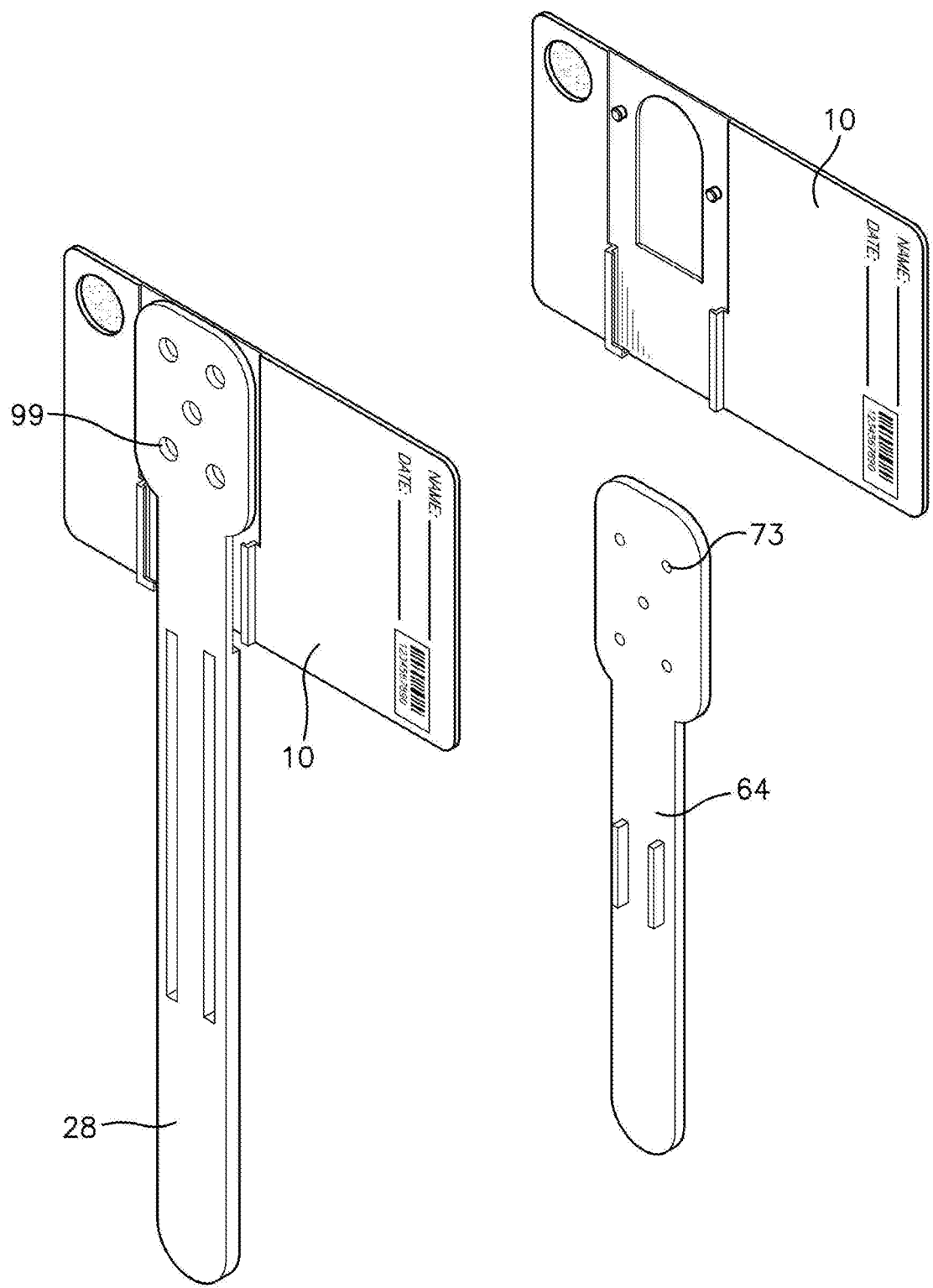
FIG. 2 is a perspective side view of the specimen collection device 100 showing the cassette 10, the slider 64 with ventilation holes 73, and handle cover 28 with ventilation holes 99.
Figure 3:
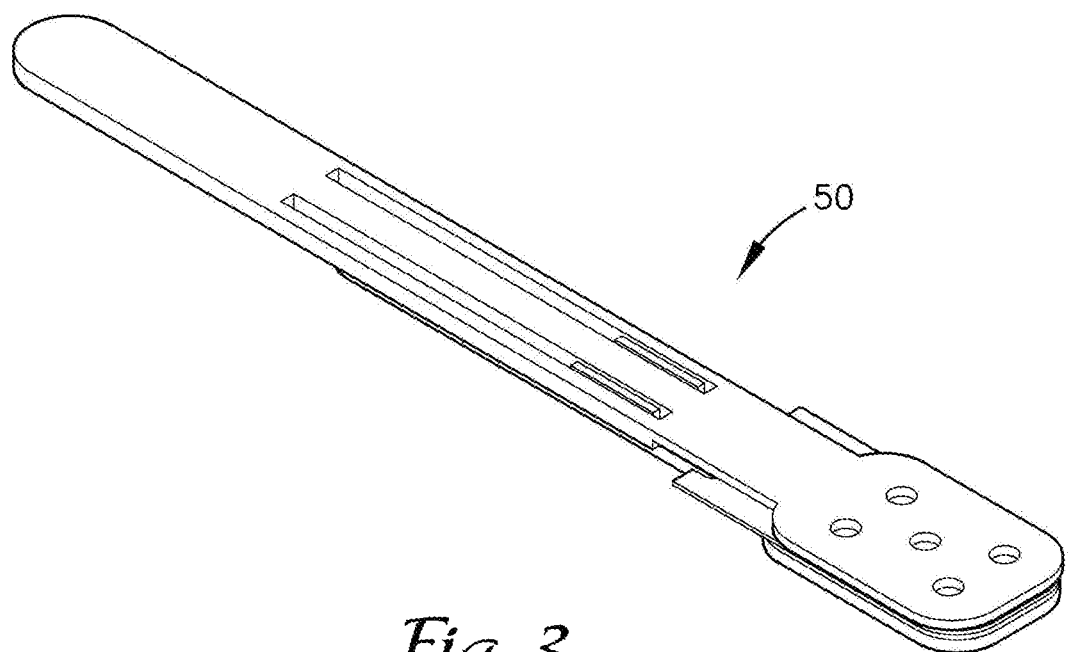
FIG. 3 is an isometric view of the specimen collector 50.
Figure 4:
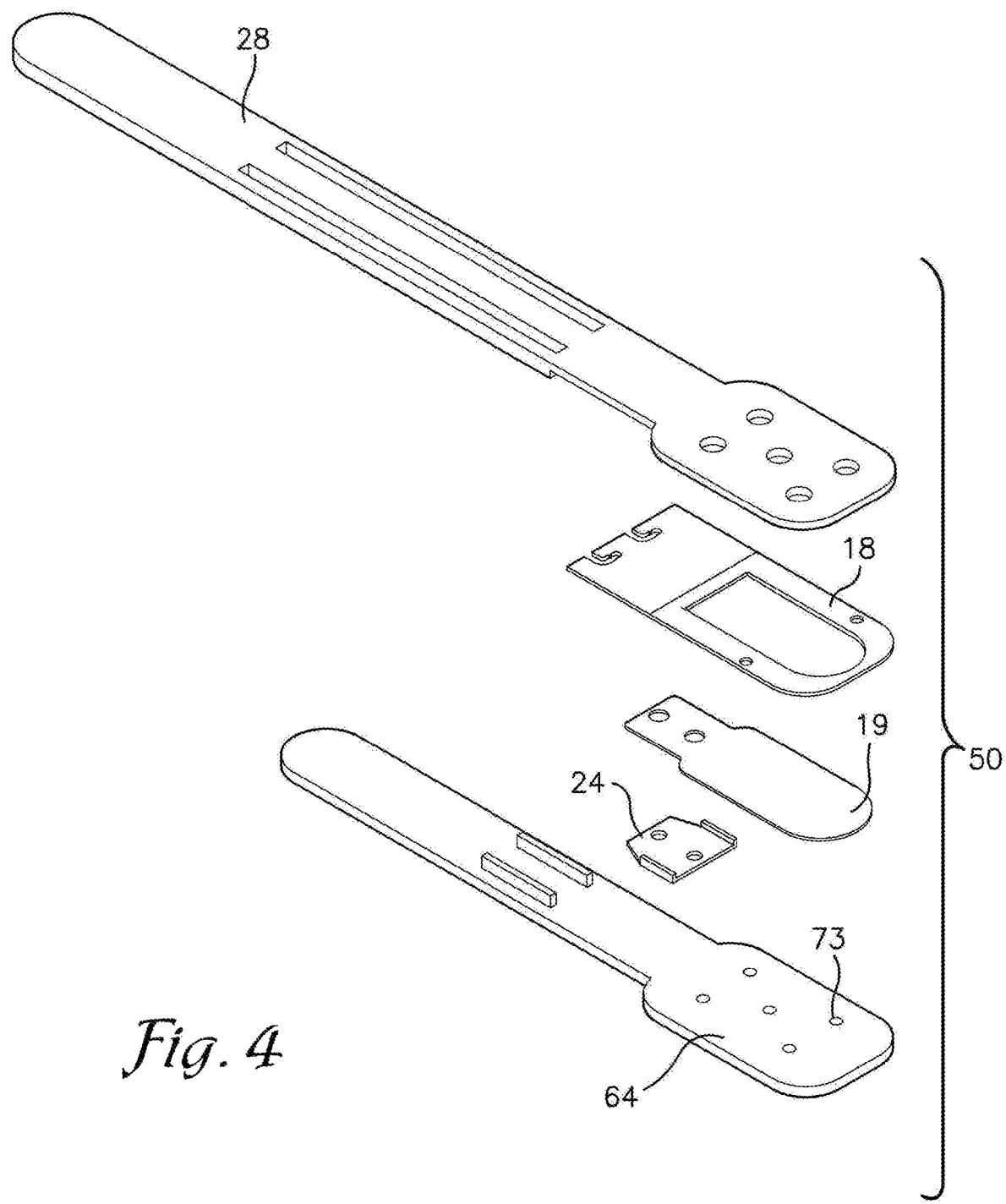
FIG. 4 is an exploded view of the specimen collector 50 showing the sample collection carrier 18, the collection absorbent 19, support cap 24, slider 64, and handle cover 28.
Figure 5:
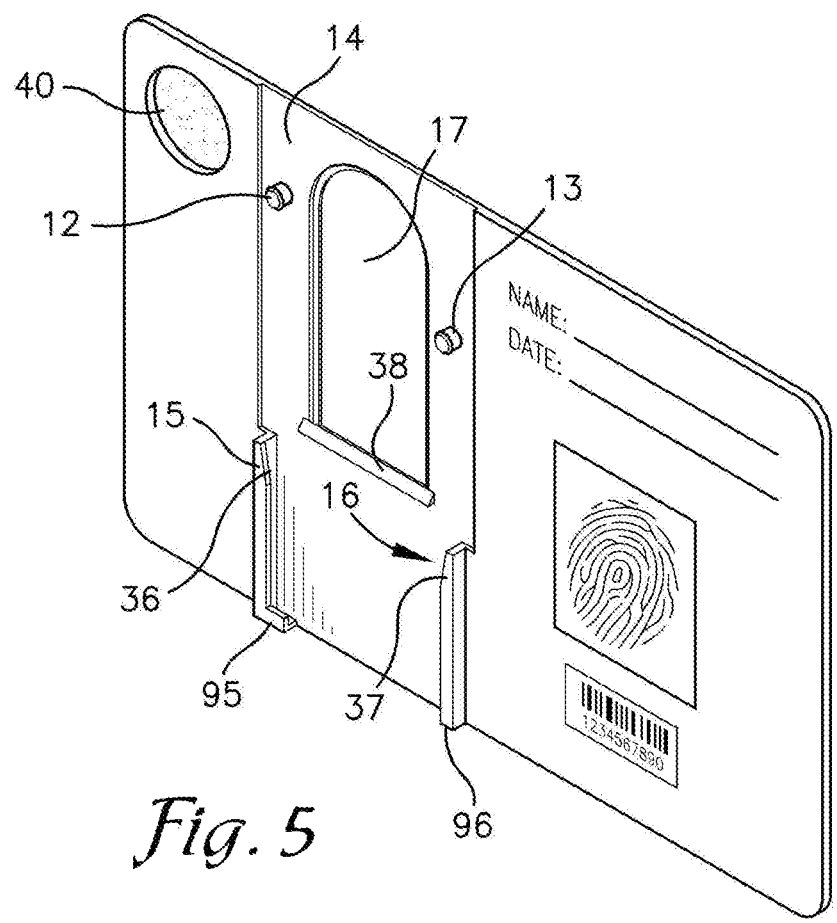
FIG. 5 is a perspective side view of the cassette 10 showing the receiver impression 14, a first collector retaining flange 15, a second collector retaining flange 16, the first and second flanges having angled ingress cuts 36 and 37, back stops 95 and 96, front stop 38, clean punch area 40, a first collector attachment peg 12 and a second collector attachment peg 13.
Figure 6:
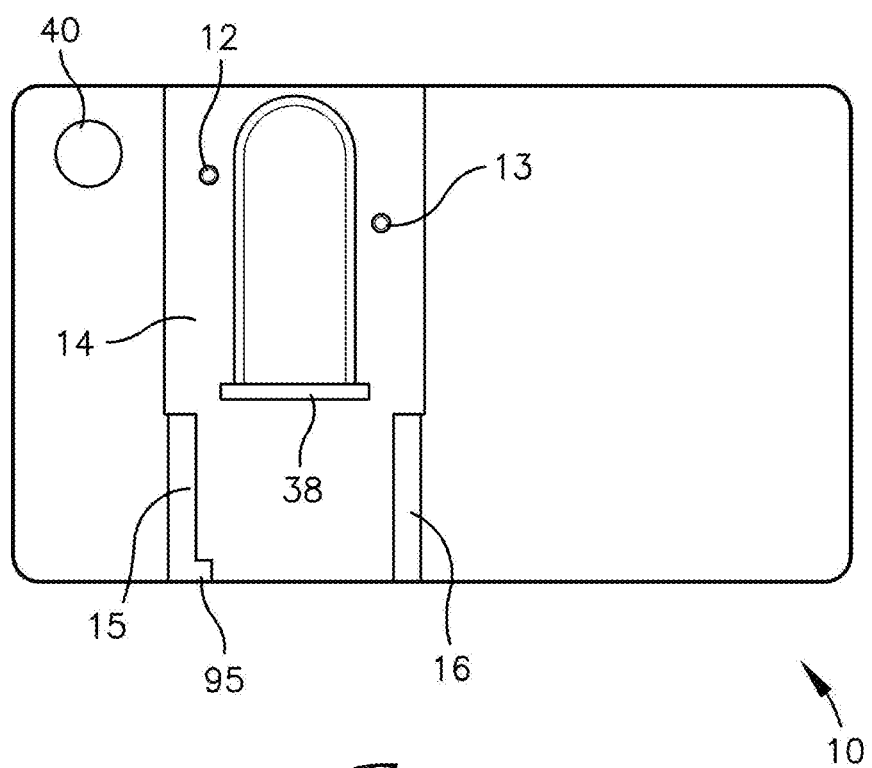
FIG. 6 is a front view of the cassette 10 showing the receiver impression 14, a first collector retaining flange 15, a second collector retaining flange 16, back stop 95, front stop 38, clean punch area 40, a first collector attachment peg 12 and a second collector attachment peg 13.
Figure 7:
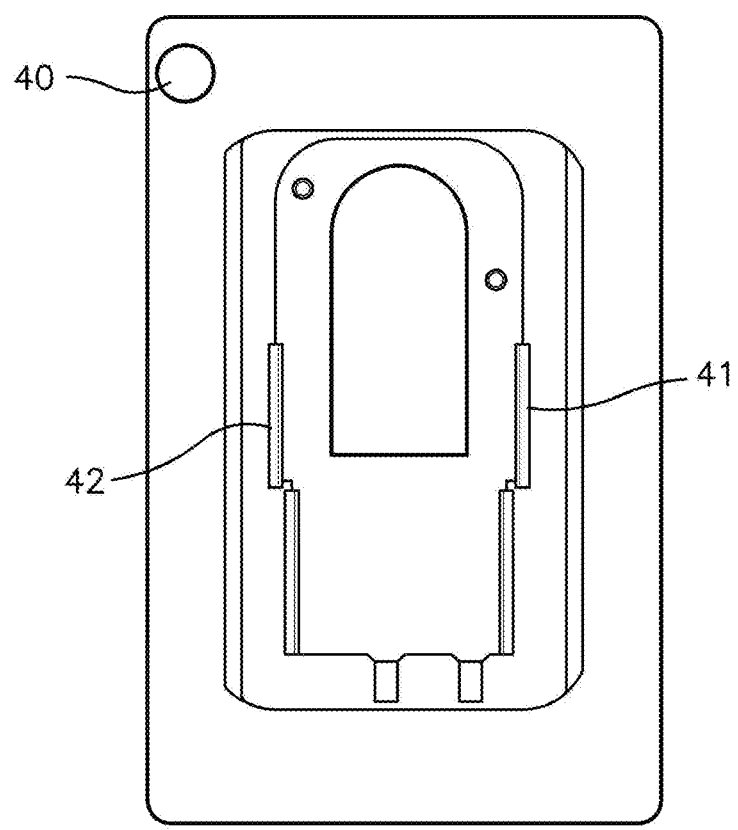
FIG. 7 is a front plan view of a cassette 10 having a clean punch area 40, and a receiver impression 14 comprising a first tamper resistant snap 41 and a second tamper resistant snap 42.
Figure 8:
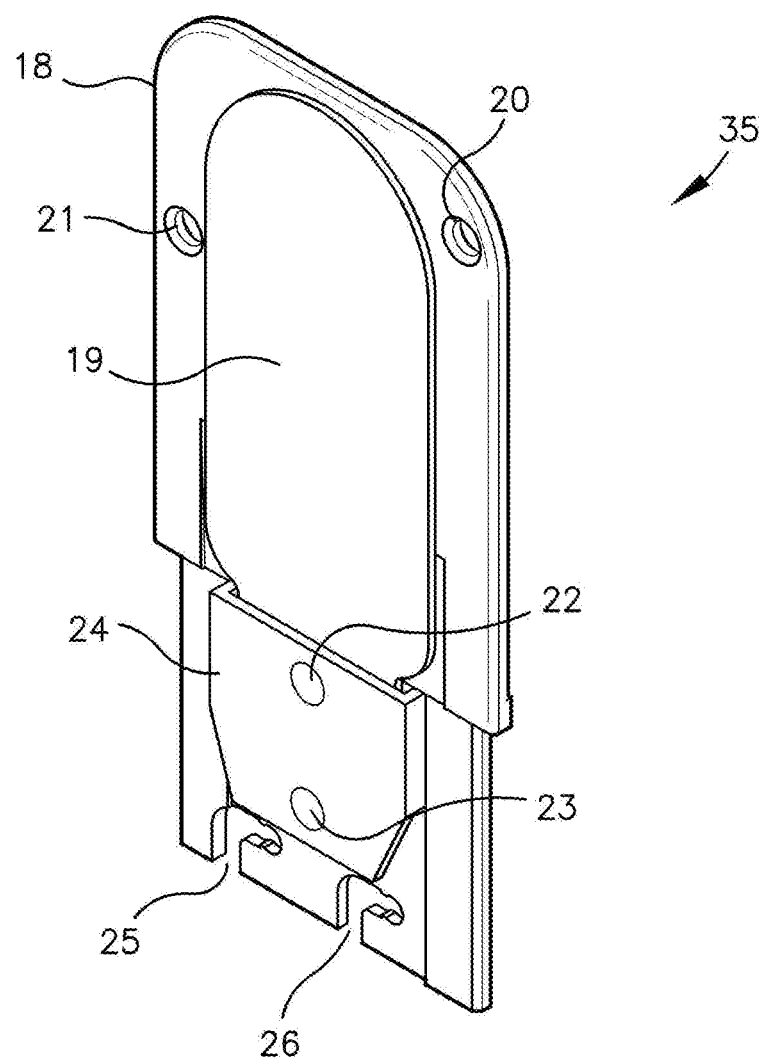
FIG. 8 is a perspective side view of a collection assembly 35 showing the sample collection carrier 18, support cap 24, the collection absorbent 19, support pegs 22 and 23, cassette attachment voids 20 and 21, and handle slots 25 and 26.
Figure 9:
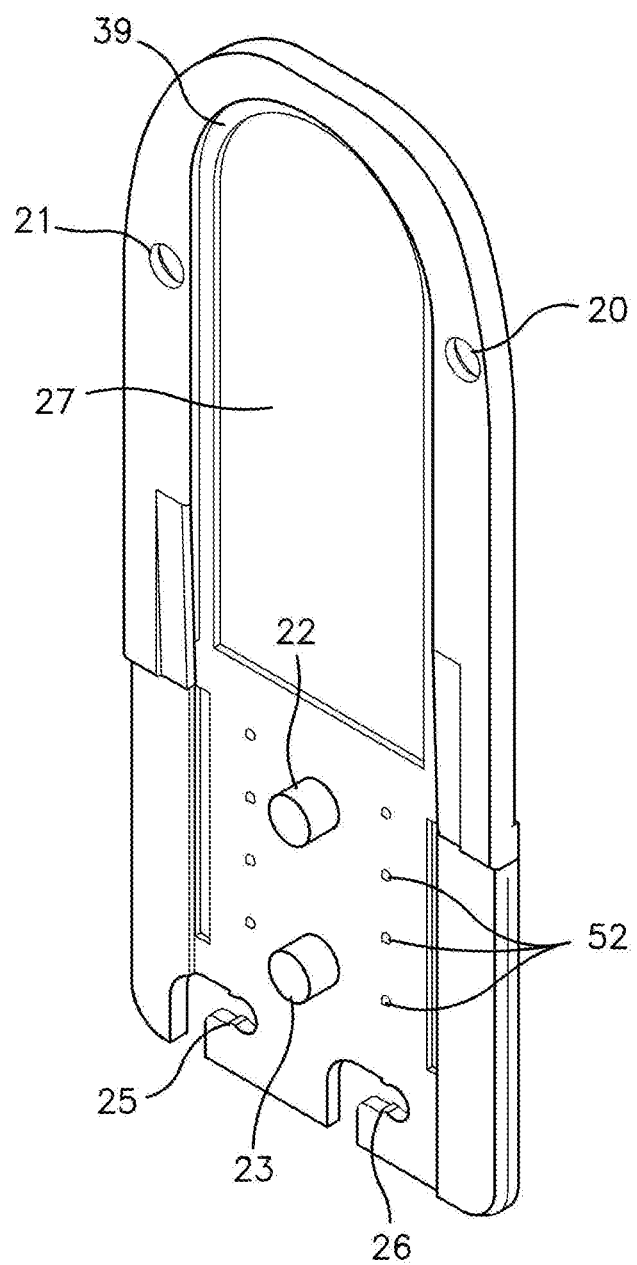
FIG. 9 is a perspective side view of a collection carrier 18 showing support pegs 22 and 23, cassette attachment voids 20 and 21, the recessed ridge 39 to accommodate the collection absorbent 19, microbumps 52, handle slots 25 and 26, and the sample access void 27.
Figure 10:
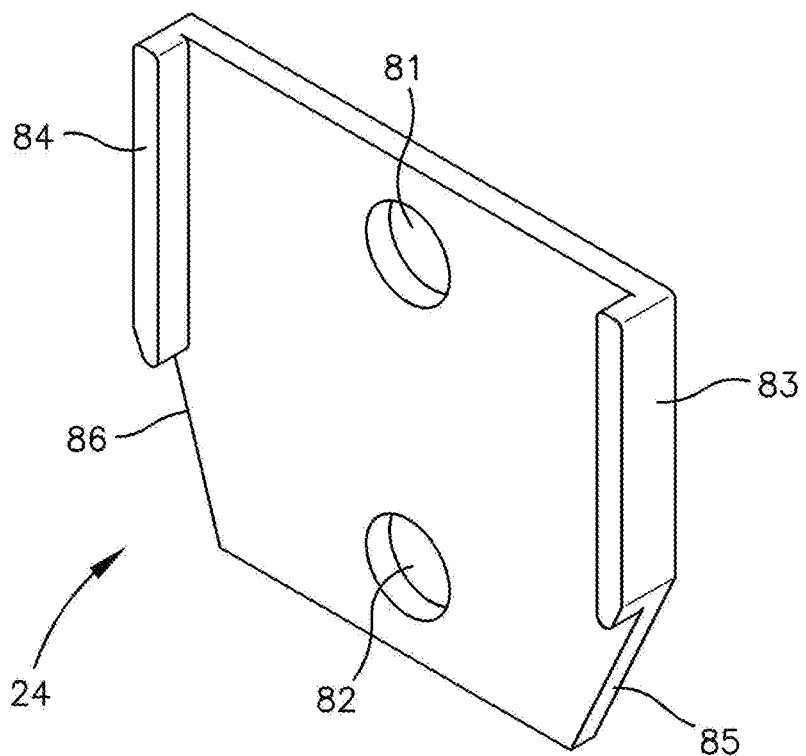
FIG. 10 is a front perspective view of the support cap 24 showing voids 81 and 82, side walls 83 and 84, and sloped ends 85 and 86.
Figure 11:
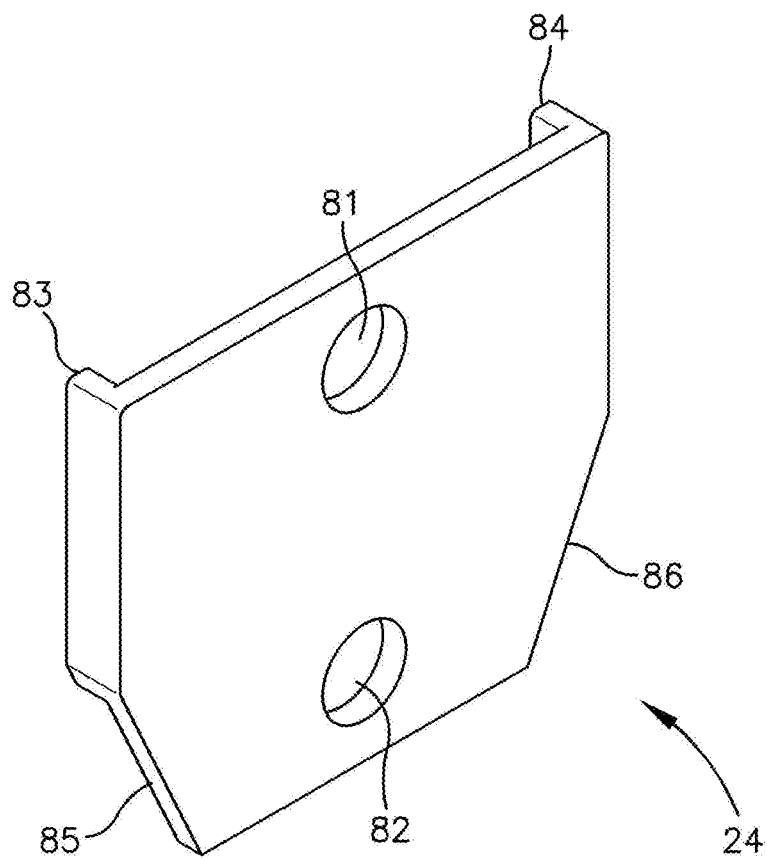
FIG. 11 is a back perspective view of the support cap 24 showing voids 81 and 82, side walls 83 and 84, and sloped ends 85 and 86.
Figure 12:
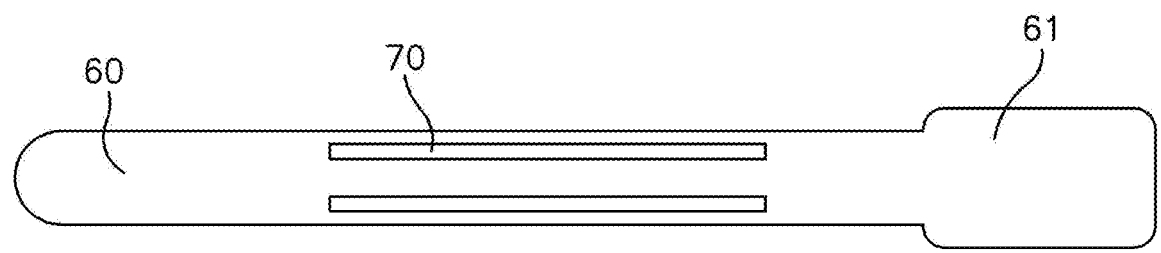
FIG. 12 is a back view of the handle cover 28 showing the handle 60 and the specimen collection support 61, and tracks 70.
Figure 13:
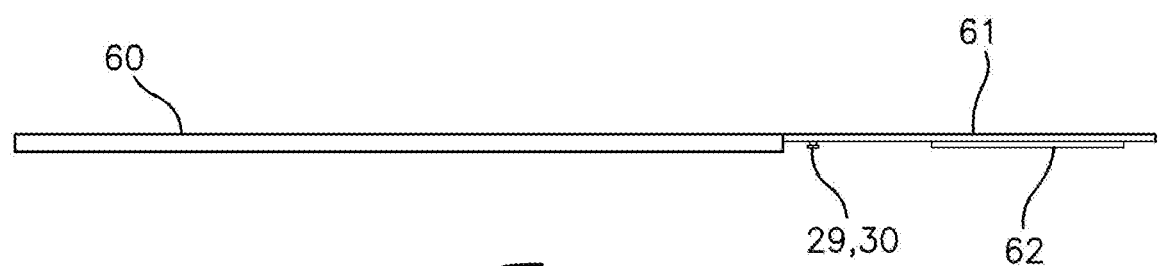
FIG. 13 is a side view of the handle cover 28 showing the handle 60 and the specimen collection support 61, carrier attachment pegs 29 and 30, and the raised portion 62.
Figure 14:
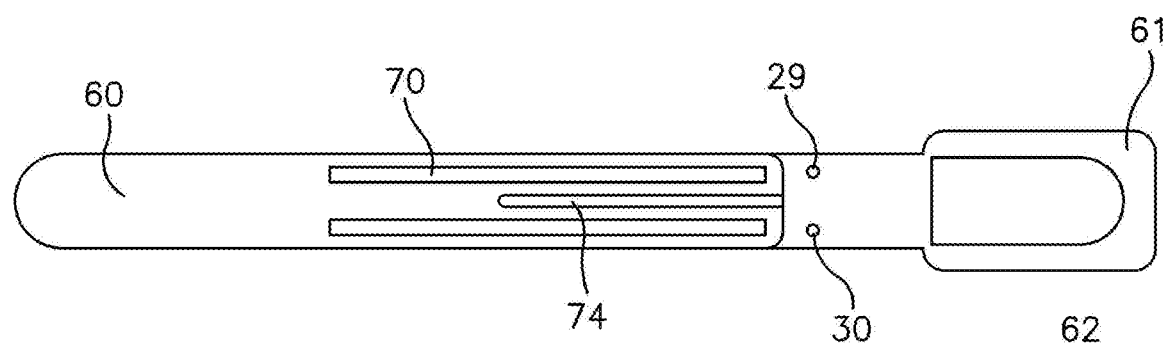
FIG. 14 is a front view of the handle cover 28 showing the handle 60 and the specimen collection support 61, tracks 70, the raised portion 62, carrier attachment pegs 29 and 30, and groove 74.
Figure 15:
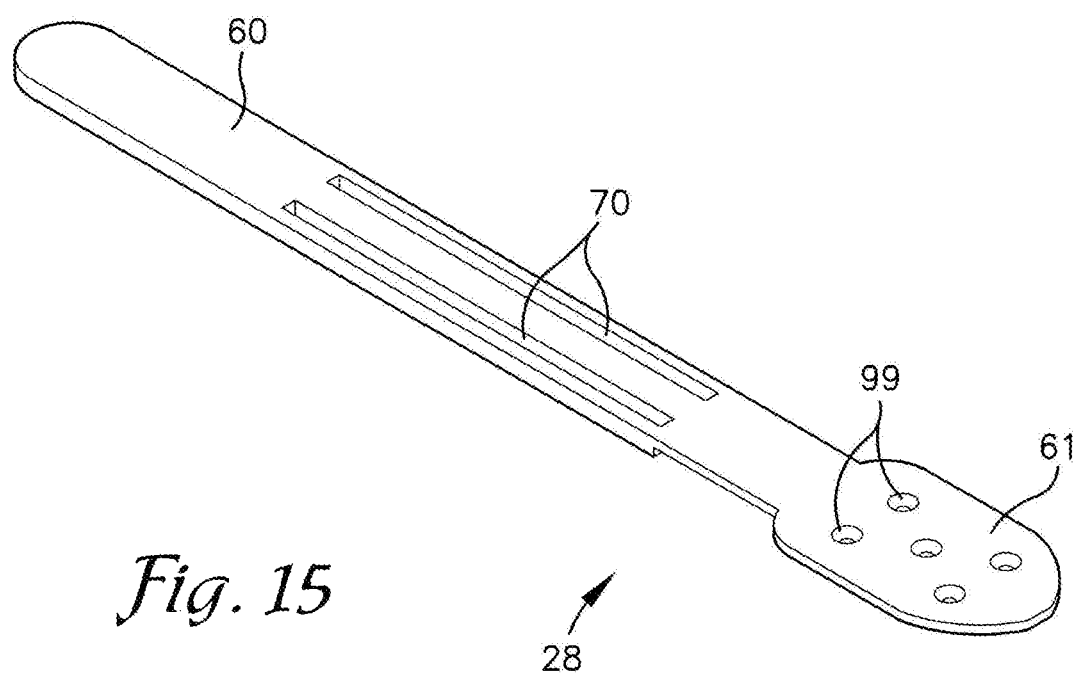
FIG. 15 is a back view of the handle cover 28 showing the handle 60 and the specimen collection support 61, tracks 70, and ventilation holes 99.
Figure 16:
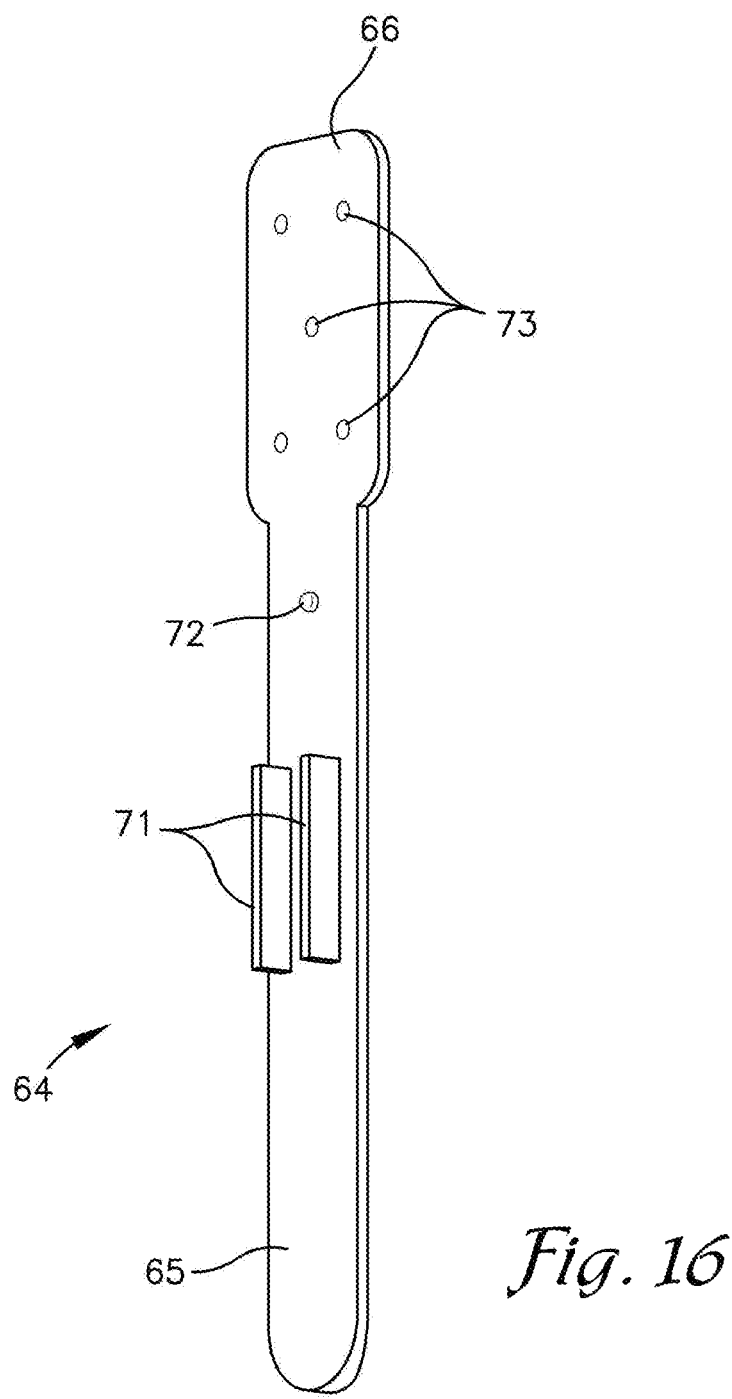
FIG. 16 is a front view of the slider 64 showing the body 65, the head 66, rails 71, protrusion 72, and ventilation holes 73.
Figure 17:
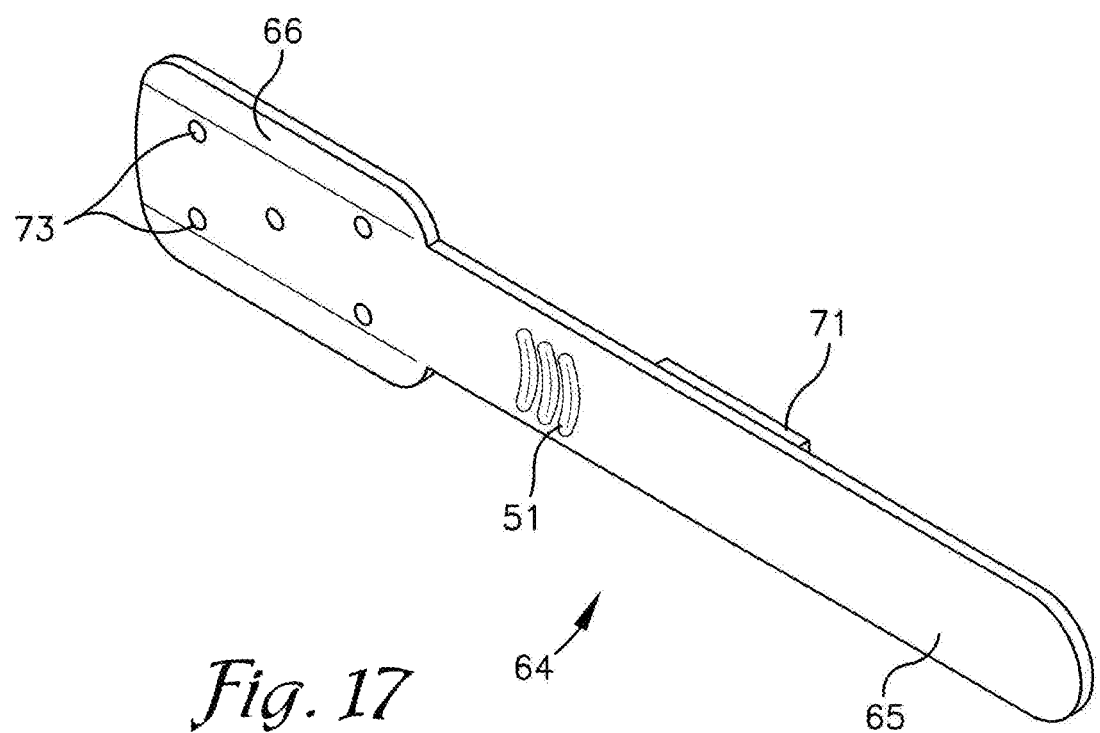
FIG. 17 is a perspective back view of the slider 64 showing the body 65, the head 66, rails 71, holding ridges 51, and ventilation holes 73.

The present invention relates to specimen collection devices used to collect biological samples in a form suitable for storage and subsequent automated analysis. The methods of use provide a safe, convenient, easy-to-use, and reliable means for collecting biological samples, and for preserving and drying the collected biological samples. The method further provides for storing collected biological samples or evidence in a manner that meets chain-of-custody requirements and provides secure evidence handling, as well as reliable accuracy of analytical results. Moreover, the invention provides for enhanced convenience and efficiency when samples are analyzed using automated systems.

The instant specimen collection device provides for the ability to apply preservative reagent to a collected biological specimen on the device to prevent deterioration of the specimen, and to provide means for ventilation for efficient evaporation and drying of the collected specimen. Efficient drying significantly enhances the preservation of the collected specimen and provides for superior forensic analysis of the specimen. The specimen collection device also incorporates the original specimen collection absorbent and avoids the need for any transfer of the specimen onto a second absorbent or requiring the transfer of a bar code or other identifying material from the collection absorbent or sample carrier or cassette or sampling device onto the sample device holder. The absorbent or sampling paper surface of the device, while held within the cassette, is exposed so that small portions or circles can be punched from the paper for delivery into testing vials for further analysis. As such, this invention provides a safe, convenient and minimally labor intensive apparatus and methods for collecting, preserving, drying, and analyzing biological samples. Further, the collection cassette of the invention provides for storage and subsequent automated analysis of the stored biological sample or evidence. Also, the present invention provides methods for using the collection cassette in the collection of biological samples or evidence in forms suitable for storage and subsequent analysis.

In several places throughout the present specification, guidance is provided through example embodiments. In each instance, the recited embodiments serve only as representative groups and are not meant to be exclusive.

A specimen collection device 100 of the instant disclosure comprises a cassette 10 and a specimen collector 50. The specimen collector 50 comprises a specimen collection assembly 35, a handle cover 28, and a slider or sliding cover 64. The specimen collection assembly 35 can be attached to the handle cover 28 for collection of the sample, and can be transferred to the cassette 10 for storage or sample analysis. Below, the cooperation of elements of the specimen collection device 100 that allow a safe, convenient and minimally labor intensive collection, preserving, drying, and analyzing biological samples will be described.

A cassette 10 of the device generally has a rectangular shape. The cassette 10 may be shaped similar to a standard credit card, having a length about 85 mm, a width about 54 mm, and a thickness of about 1 mm. In some embodiments, the cassette 10 may also have a length of about 30, 35, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 mm or more. In other embodiments, the cassette 10 has a thickness of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 mm or more. In an alternative of the embodiments, the cassette 10 has a length ranging from about 30 mm to about 90 mm. In some aspects, the cassette 10 has a width ranging from about 30 mm to about 90 mm. In some aspects, the cassette 10 has a thickness ranging from about 0.1 mm to about 3.0 mm. In another alternative of the embodiments, the cassette 10 has a length ranging from about 50 mm to about 85 mm, a width ranging from about 50 mm to about 85 mm, and a thickness ranging from about 0.5 mm to about 2.5 mm. In yet another alternative of the embodiments, the cassette 10 has a thickness of about 0.8 mm to about 1.5 mm, a length of about 80 mm to about 85 mm, and a width of about 50 mm to about 55 mm. In an alternative of the embodiments, the cassette 10 has a thickness of about 0.8 mm to about 1.5 mm, a length of about 50 mm to about 55 mm, and a width of about 50 mm to about 55 mm. In an additional alternative of the embodiments, the cassette 10 has a length of about 53 mm and a width of about 53 mm. In an alternative of the embodiments, the cassette 10 has a length of about 85 mm and a width of about 53 mm. The cassette shape may be optimized for use in automated handling.

The cassette 10 comprises a receiver impression 14 therein. The receiver impression 14 includes an access void 17 that registers with an access void 27 and a collection absorbent 19 of the collection assembly 35 when the sample collection carrier 18 is attached to the cassette 10. The receiver impression 14 includes means for attaching the collection assembly 35 for maintaining a secure fit of the collection assembly 35 in the cassette 10 for storage and for immobilizing the collection assembly 35 during automatic punching of the sample. The collector attachment means may be any attachment means or combination of attachment means known in the art that secures the sample collection carrier 18 of the collection assembly 35 to the cassette 10 such that the collection absorbent 19 aligns with the receiver impression 14 and access void 17. Such collector attachment means include, without limitation, a plurality of pegs and respective voids for press fitting the sample collector to the cassette, flanges, and stops.

In some embodiments, the collector attachment means of the receiver impression 14 comprises a first collector retaining flange 15 and a second collector retaining flange 16. The collector retaining flanges assist in the alignment of the sample collection carrier 18 with the receiver impression 14 of the cassette, as well as the attachment of the sample collection carrier 18 to the cassette 10. In a preferred embodiment, the first collector retaining flange 15 and the second collector retaining flange 16 have angled ingress cuts 36 and 37 to facilitate insertion of the collection assembly 35 into the cassette 10. The first collector retaining flange 15, the second collector retaining flange 16, or both may further comprise back stops 95 and 96 for retaining the collection assembly 35 within the cassette, prevent the collection assembly 35 from sliding out of the cassette, and facilitate positioning the collection assembly 35 in the receiver impression 14. In a preferred embodiment, the first collector retaining flange 15 comprises a back stop 95.

In some embodiments, the collector attachment means of the receiver impression 14 may comprise a support cap void 55 that registers with, and engages the elevated support cap 24 of the collection assembly 35 when the sample collection carrier 18 is attached to the cassette 10.

In some embodiments, the collector attachment means of the receiver impression 14 comprise a front stop 38 for retaining the collection assembly 35 within the cassette, prevent the collection assembly 35 from sliding out of the cassette, and facilitate releasing the handle cover 28 from the sample collection carrier 18 of the collection assembly 35. In a preferred embodiment, the front stop is angled to facilitate insertion of the collection assembly 35 into the cassette 10, but prevent the collection assembly 35 from sliding out of the cassette.

In some embodiments, the collector attachment means of the receiver impression 14 comprises a first collector attachment void and a second collector attachment void that correspond to a first collector attachment peg and a second collector attachment peg on the collector. In other embodiments, the collector attachment means of the receiver impression 14 comprises a combination of collector attachment voids and corresponding collector attachment pegs. In preferred embodiments, the collector attachment means of the receiver impression 14 comprises a first collector attachment peg 12 and a second collector attachment peg 13 that correspond to a first collector attachment void 20 and a second collector attachment void 21 on the collector.

Preferably, the collector attachment means of the receiver impression 14 comprises a first collector retaining flange 15 and a second collector retaining flange 16, a support cap void 55 that registers with, and engages the elevated support cap 24 of the collection assembly 35, attachment voids or pegs, and front stops. When the collector attachment means of the receiver impression 14 comprises retaining flanges, a support cap void, attachment voids or pegs, and front stops, the attachment means conspire to provide a substantially more secure attachment of the collection assembly 35 to the cassette 10, thereby ensuring enhanced chain-of-custody requirements and more secure evidence handling.

In some embodiments, the cassette 10 may further comprise a plurality of indentations, such as a first indentation 56 and a second indentation 57, which provide access for a plurality of carrier attachment pegs on the handle 28, such as a first carrier attachment peg 29 and a second carrier attachment peg 30, after the specimen collection assembly 35 is attached to the cassette 10, and during removal of the handle cover 28 specimen collection assembly 35.

The access void 17 of the cassette 10 may be covered or encased in a protective material, for example, a plastic film, which may further protect against degradation and contamination of collected biological samples. Suitable plastic films or protective material are known in the art and may include polystyrene, polyethylene, polypropylene and other suitable lamination plastics.

In some aspects, the cassette 10 includes a clean punch area 40. Suitable clean punch areas provide a material that is used as the collection absorbent, but is free from collected specimen. The clean punch area is used to clean a punch apparatus between punches taken from the collection absorbent for downstream specimen analysis. The clean punch area 40 may be located anywhere on the cassette that is compatible for use by automated analysis equipment and that does not interfere with the collection absorbent or identification indicia.

The cassette 10 may further include tamper resistant attachment means that attach the sample collection carrier to the cassette such that attempts to separate the sample collection carrier from the cassette are prevented or indicated. Such tamper resistant attachment includes such tamper resistant attachment means known in the art and may include tamper resistant seals, tampering indication dyes, and tamper resistant snaps. In some aspects, the cassette 10 includes tamper resistant snaps, where the cassette 10 includes a first tamper resistant snap 41 and a second tamper resistant snap 42. Such tamper resistant snaps allow the sample collection carrier to be press fit into the cassette and hinder the removal of the sample collection carrier from the cassette without noticeable damage to the device.

Aspects of the invention also include a specimen collector 50 having a collection assembly 35, a handle cover 28, and a slider or sliding cover 64. The collection assembly 35 comprises a sample collection carrier 18, a collection absorbent 19 attached thereon, a means for attaching the collection absorbent 19 to the sample collection carrier 18 using a support cap 24, a sample access void 27, a recessed ridge 39 to accommodate the collection absorbent 19, and a means for attaching the sample collection carrier 18 to the handle cover 28. The sample access void 27 of the sample collection carrier 18 aligns with the access void 17 within the receiver impression 14 of the cassette 10.

The collection absorbent 19 of the sample collection carrier 18 is capable of attaching to at least one biological sample or evidence and for storing such biological sample or evidence. The collection absorbent 19 is attached to the sample collection carrier 18 such that the collection absorbent is locked into the sample collection carrier and cannot be removed. The sample collection carrier 18 may further comprise microbumps 52 to prevent sliding of, and aid in stabilizing the collection absorbent 19 on the sample collection carrier 18. In some embodiments, the attachment means is tamper proof. In some embodiments, the attachment means causes detectable damage if it has been tampered with. Suitable attachment means include those that prevent the absorbent collector 19 from being detached from the sample collection carrier 18 once it is initially attached. For example, an attachment means may include sonic welding of the collection absorbent 19. In preferred embodiments, the attachment means includes a first support peg 22, a second support peg 23, and the support cap 24, with the support cap 24 having voids 81 and 82 that register with the first and second support pegs. Further, the support cap 24 is attached to the first and second support pegs (22 and 23) by sonic welding. The support cap 24 further comprises side walls 83 and 84 to accommodate the collection absorbent 19, and provide sufficient elevation to engage a protrusion 72 on the slider 64 and raise the head 66 of the slider 64 above the collection absorbent 19, thereby creating a ventilation gap between the head 66 and the collection absorbent 19. In preferred embodiments, the bottom ends 85 and 86 are sloped to facilitate insertion of the collection assembly 35 into the cassette 10.

The collection absorbent 19 may be any material to which biological samples or evidence will sorb and which does not inhibit storage or subsequent analysis of the biological sample or evidence. In one aspect, the collection absorbent 19 is of a porous nature to provide entrainment of macromolecules of the biological sample or evidence onto the collection absorbent 19. Material suitable for this purpose includes, but is not limited to, a matrix which is cellulose based (e.g., cellulose, nitrocellulose or carboxymethylcellulose), hydrophilic polymers including synthetic hydrophilic polymers (e.g., polyester, polyamide, carbohydrate polymers), polytetrafuroethylene, fiberglass, and porous ceramics.

In some embodiments, the sample collection carrier 18 may include a cover 43 for protecting the collection absorbent 19. The cover 43 attaches to the sample carrier through an attachment means. The attachment means may be any attachment means known in the art that can removably connect the cover to the sample carrier. By way of example, without limitation, the attachment means may be by a first attachment means 48 and a second attachment means 49 that press fit on the support cap attachment means. The cover 43 may be used by the user to press down on the collection absorbent 19 to press fit the sample carrier into the cassette 10. Also, the cover 43 may be used by the user to press the collection absorbent 19 into contact with a preservative substance if present. The cover 43 allows the user to press the collection absorbent 19 without introducing possible contamination to the collection absorbent.

Additives may be included on the collection absorbent 19 or added to the collection absorbent 19 after specimen collection. The additives may be located in the receiver impression 14 of the cassette 10, or on a film or covering that traverses the access void 17 of the cassette such that when the sample carrier 18 is attached to the cassette 10 the additives contact the collection absorbent 19. In some aspects, the additives may be administered directly to the collection absorbent 19 by automatic or mechanical means. The additives may be in liquid, solid, semi-solid, or film form.

The additives may include additional compositions to preserve the biological sample or evidence that are useful in downstream analyses, or inactivate potential pathogens. By way of example, additives may include one or more of a weak base, a chelating agent, a protein denaturant such as an anionic detergent, a surfactant, or free radical traps such as uric acid or a urate salt. Suitable weak bases include organic and inorganic bases.

Additives may include additional components which function in subsequent analysis to be performed on the collected biological samples or evidence. Subsequent analysis which may be performed includes methods and techniques known in the art. Such analyses include gel electrophoresis, polymerase chain reaction (PCR) based analysis, reverse transcriptase initiated PCR, ligase chain reaction (LCR), DNA or RNA hybridization techniques, restriction fragment length polymorphism (RFLP), sequencing, direct sequencing, enzymatic assays, affinity labeling, methods of detection using labels or antibodies, and other methods known in the art or yet to be discovered. Non-limiting examples of additive formulations that may be used to preserve a collected specimen may be as described in U.S. patent application Ser. No. 14/807,406, the disclosure of which is incorporated herein in its entirety.

The means for attaching the sample collection carrier 18 to the handle cover 28 may be any attachment means known in the art that secures the sample collection carrier 18 to the handle cover 28. Such carrier attachment means includes, without limitation, a plurality of pegs and/or slots on the sample collection carrier 18, wherein the plurality of pegs and/or slots are mateable with respective voids or slots on the handle cover 28. In some embodiments, the sample collection carrier 18 includes a plurality of handle pegs which are mateable with a plurality of carrier attachment slots on the handle 28. In other embodiments, the sample collection carrier 18 comprises a combination of carrier attachment pegs and handle slots which are mateable with a plurality of carrier attachment pegs and handle slots on the handle 28. In preferred embodiments, the sample collection carrier 18 includes a plurality of handle slots, such as a first handle slot 25 and a second handle slot 26, which are mateable with a plurality of carrier attachment pegs, such as a first carrier attachment peg 29 and a second carrier attachment peg 30 on the handle cover 28. When means for connecting the sample collection carrier 18 to the handle cover 28 comprises a plurality of mateable pegs and/or slots on the sample collection carrier 18 and on the handle 28, the carrier attachment pegs are tapered or beveled such that the pegs can only exit the recipient handle slot at the entry point of the handle slot. In particular, the handle slot width is smaller than the largest diameter of the peg and larger than the smallest diameter of the peg such that the peg can slide along the slot.

The handle cover 28 of the specimen collector 50 comprises a handle 60 and a specimen collection support 61 attached on one end of the handle 60. The front of the specimen collection support 61 comprises a raised portion 62 of substantially the same shape and size as the sample access void 27 of the sample collection carrier 18. Additionally, the raised portion 62 of the handle cover 28 aligns with the access void 17 within the sample access void 27 of the sample collection carrier 18. When the sample collection carrier 18 is connected to the handle cover 28, the handle 60 and the specimen collector support 61 provide a means for an operator to insert the sample collection carrier 18 into a subject's oral cavity without the user's appendages entering the subject's oral cavity. Further, the raised portion 62 of the specimen collection support 61 provides support for the sample collection carrier 18 and the collection absorbent 19 during operation such that the sample collection carrier 18 and the collection absorbent 19 can be passed along the inner oral cavity multiple times allowing pressure to be applied without user appendage penetration in the oral cavity. In preferred embodiments, the specimen collection support 61 of the handle cover 28 comprises a plurality of ventilation holes 99 to facilitate drying of a collected sample. The holes 99 may further be used to apply preservative additives to the collected specimen on the collection absorbent 19 to preserve the biological sample or evidence, or inactivate potential pathogens.

The slider or sliding cover 64 of the specimen collector 50 comprises a body 65 and a head 66. The body 65 of the slider 64 is substantially the same width as the width of the handle 60 of the handle cover 28, and the head 66 of the slider 64 is substantially the same size and shape as the specimen collection support 61 of the handle cover 28. In preferred embodiments, the head 66 of the slider 64 comprises a plurality of ventilation holes 73 to facilitate drying of a collected sample.

In some embodiments, the slider head 66 of the slider 64 further comprises protrusions 54a and b attached to the interior side of the slider head 66. The protrusions 54a and b are on each side of the raised portion 62 of the specimen collection support 61 and in register with the collector attachment voids 20 and 21 of the sample collection carrier 18. The protrusions 54a and b may be the same size as the collector attachment voids 20 and 21. Alternatively, the protrusions 54a and b may be larger than the collector attachment voids 20 and 21. Additionally, the protrusions 54a and b may be solid. Preferably, the protrusions 54a and b are hollow.

The slider 64 of the specimen collector 50 is removably and slidably mounted on the handle cover 28 and slides within tracks 70, which tracks 70 receive rails 71 of the slider 64. The slider 64 is capable of moving forwardly and backwardly on the handle cover 28 to either expose or to cover the entire sample collection carrier 18 and collection absorbent 19 attached thereon. As such, when moved backwardly, the slider 64 allows for a specimen to be collected and provides additional strength and support for the handle cover 28 during specimen collection. When moved forwardly, the slider 64 provides protection for the collected specimen. Further, when moved backwardly, the slider 64 allows for the application of the preservative additives to the collected specimen on the collection absorbent 19. Alternatively, when moved forwardly, the holes 73 of the slider 64 may be used to apply preservative additives to the collected specimen on the collection absorbent 19 to preserve the biological sample or evidence, or inactivate potential pathogens.

The slider 64 further comprises an additional means for providing ventilation for efficient evaporation and drying of the collected specimen. The additional means for ventilation comprises a protrusion 72 on the interior side of the body 65 of the slider 64. When the slider 64 is moved backwardly, the protrusion 72 registers with, and slides within a groove 74 on the interior side of the handle cover 28. However, when the slider 64 is moved forwardly to place the head 66 of the slider 64 over the sample collection carrier 18 and collection absorbent 19 attached thereon, the protrusion 72 engages the elevated support cap 24 of the collection assembly 35, thereby raising the head 66 of the slider 64 above the collection absorbent 19 and creating a ventilation gap between the head 66 and the collection absorbent 19.

The slider 64 may further include holding ridges 51 for aiding the user in holding and sliding the slider 64 of the specimen collector 50 along the length of the handle cover 28. Such holding ridges may be of any means known in the art for providing friction between the slider 64 and a user's appendage. By way of example, without limitation, the holding ridges 51 may be a series of ridges or bumps that are raised above the surface of the slider 64.

Figure 18:
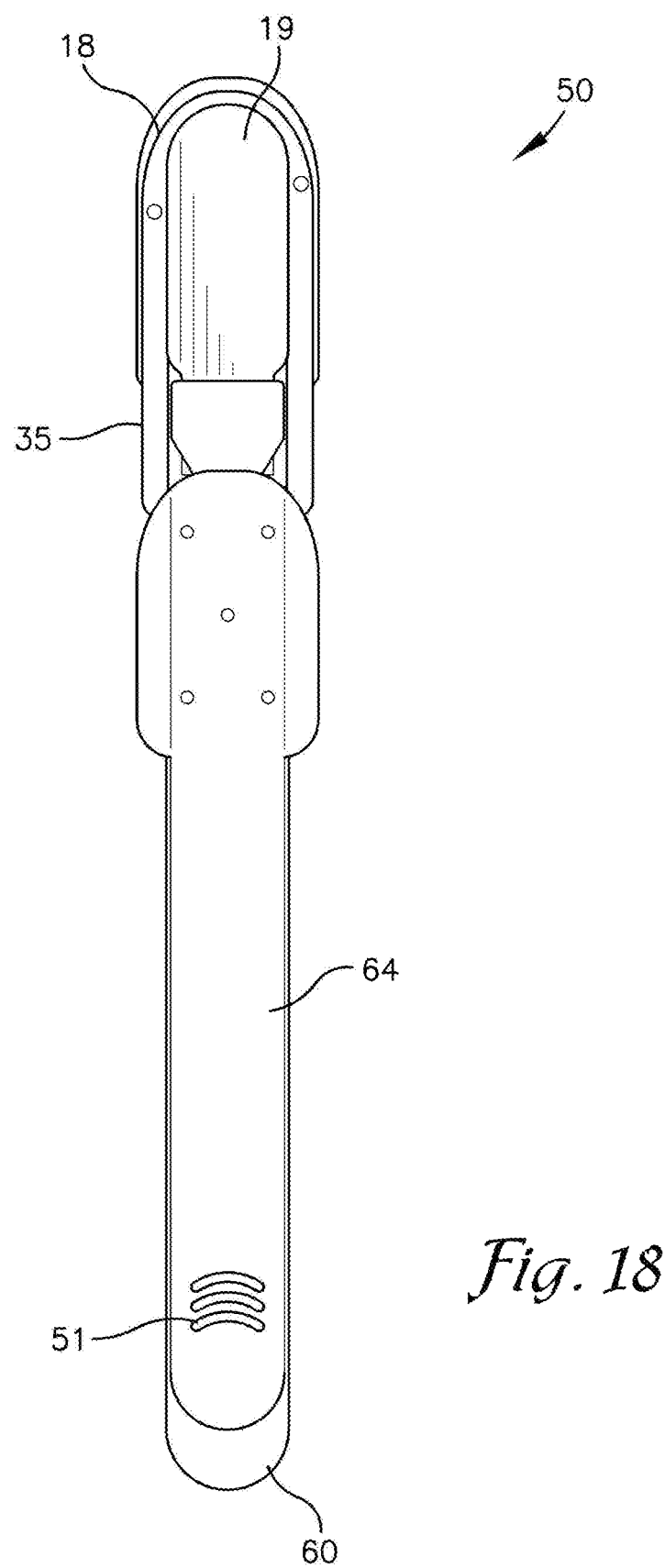
FIG. 18 is a front view of the specimen collector 50 showing the slider 64 in a lowered position, exposing the collection absorbent 19 attached to the collection carrier 18 of the specimen collection assembly 35.
Figure 19:
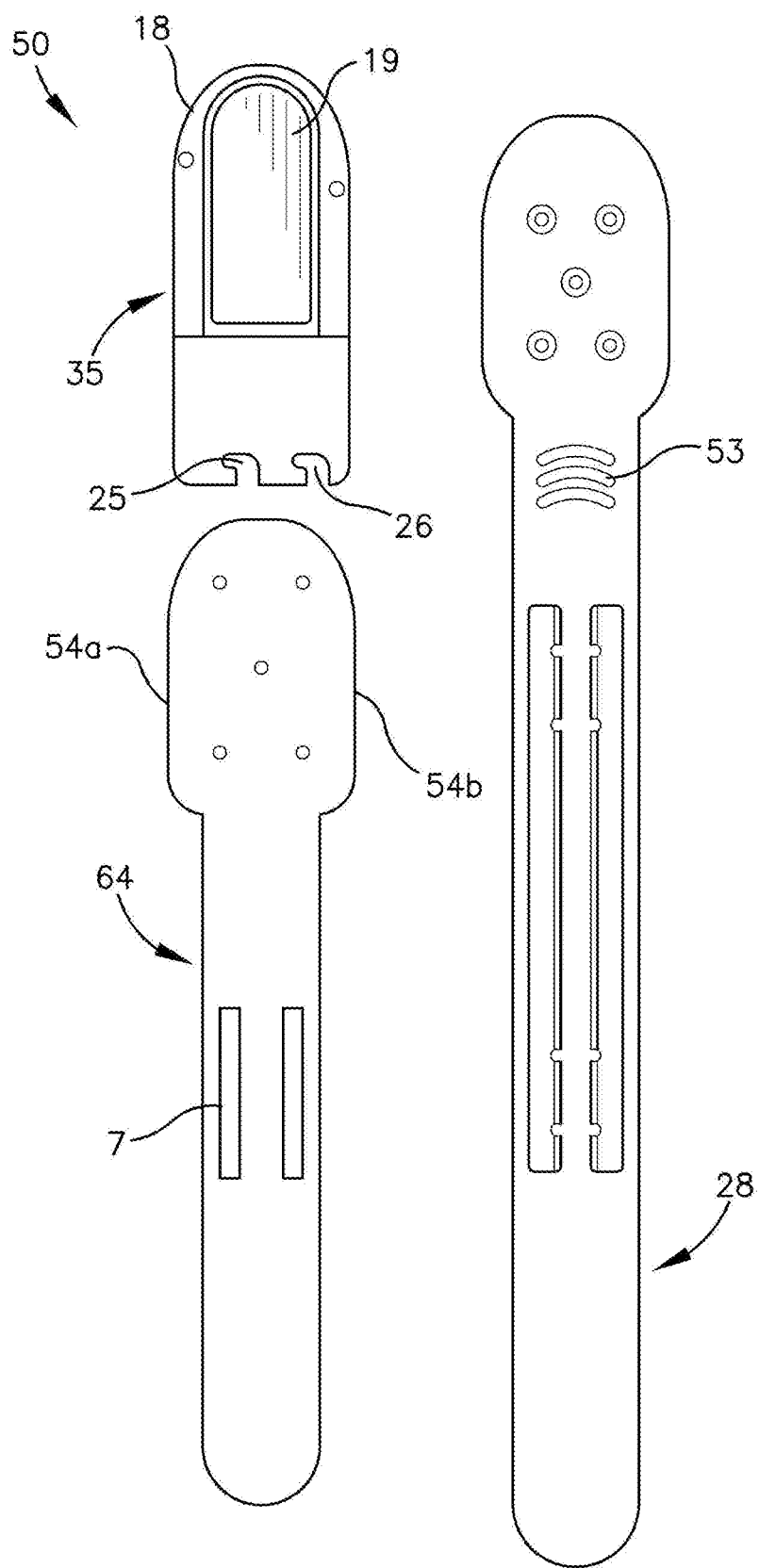
FIG. 19 is a disassembled specimen collector 50 showing a back side view of slider 64 and rails 7 and protrusions 54a and b on the interior side of slider 64, the collection assembly 35 with the collection carrier 18 and the collection absorbent 19 attached thereon and showing handle slots 25 and 26, and the handle cover 28.
Figure 20:
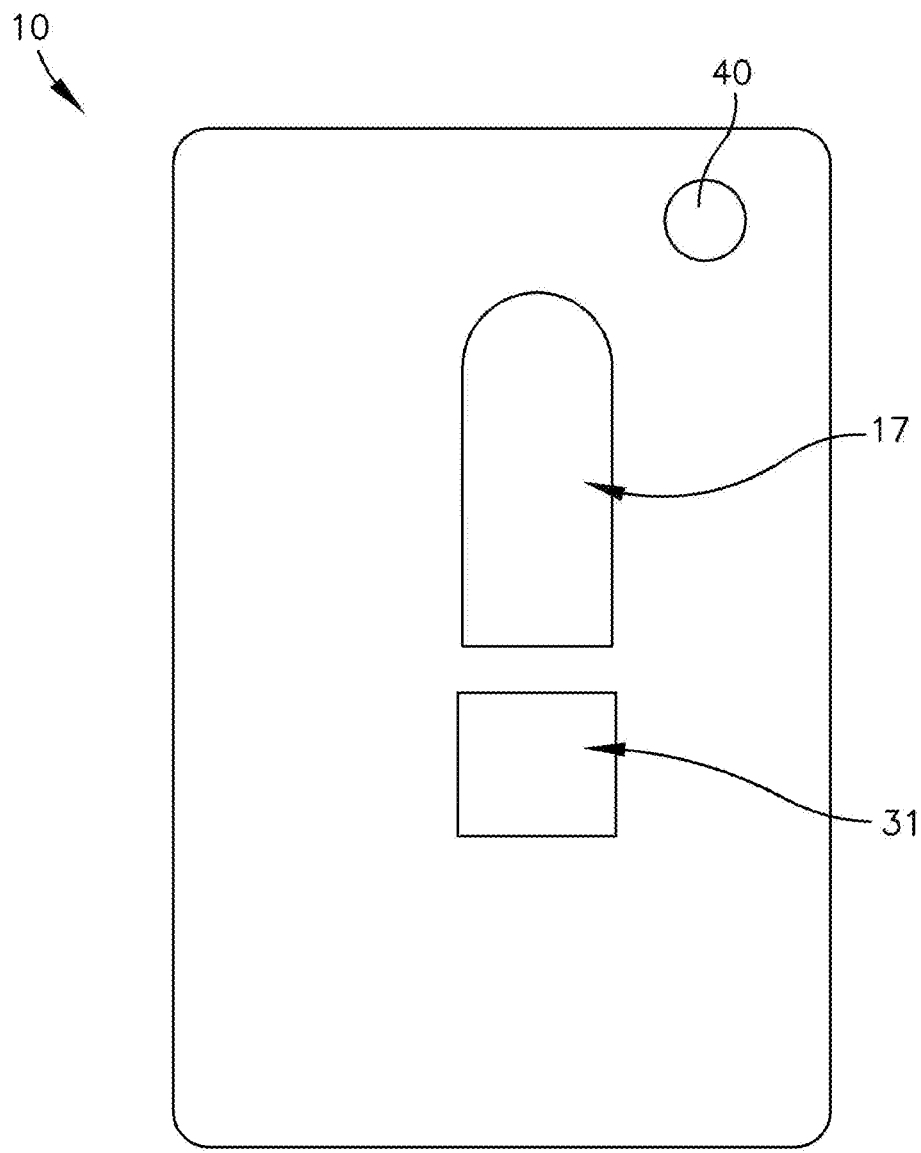
FIG. 20 is a front view of an embodiment of a cassette 10 having a clean punch area 40 and having a support cap void 31 mateable with a support cap 24 of a collection carrier 18.
Figure 21:
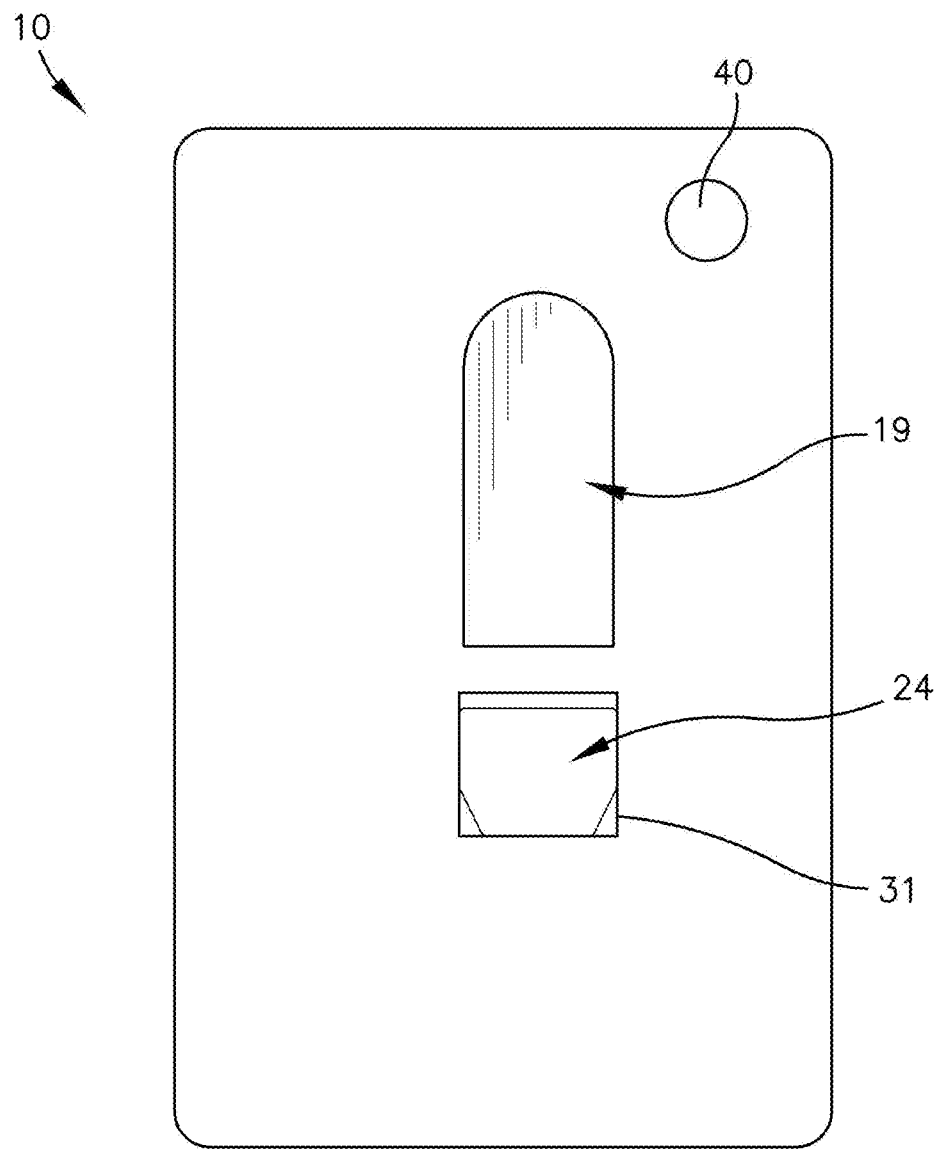
FIG. 21 is a back view of cassette 10 having a collection assembly 35 (not fully visible) attached thereon, and showing a collection absorbent 19 attached onto the collection assembly 35. The support cap 24 of collection assembly 35 is visible wedged in the void 31 of the cassette 10. A clean punch area 40 is also visible.
Figure 22:
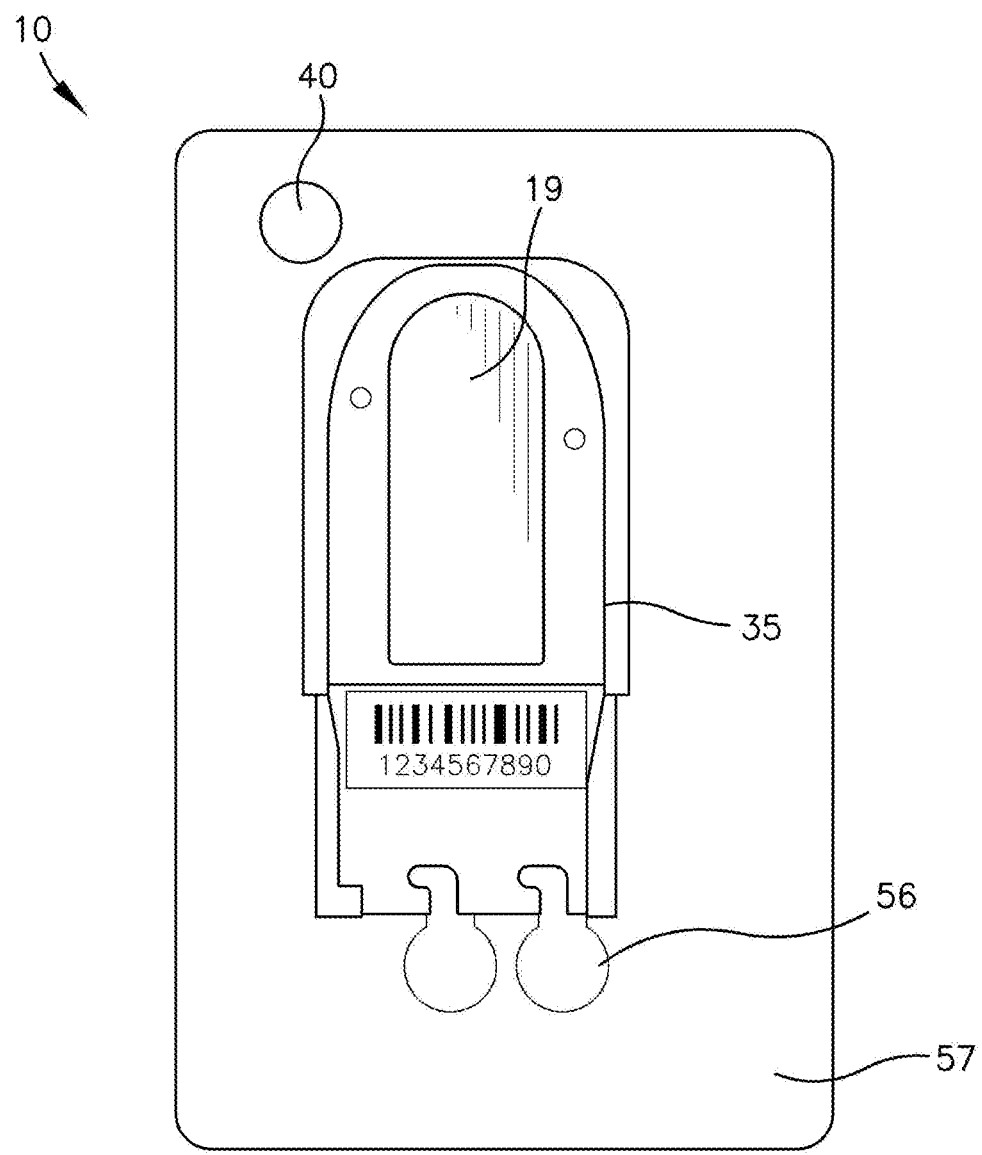
FIG. 22 is a front view of cassette 10 having a collection assembly 35 attached thereon, and showing a collection absorbent 19 attached onto the collection assembly 35, and a clean punch area 40. A first impression 56 and a second impression 57 are also visible.

Referring now to FIGS. 18-22, an embodiment of a specimen collection device 100 will be described. FIG. 18 shows a front view of an embodiment of an assembled specimen collector 50 showing the slider 64 with holding ridges 51. The slider 64 is moved backwardly and in a lowered position, exposing the collection absorbent 19 attached to the collection assembly 35 in the collection carrier 18. The handle 60 of the handle cover 28, partially covered by the slider 64 is also visible. FIG. 19 shows a disassembled specimen collector 50, showing the reverse side of the slider 64, with the rails 7 and protrusions 54a and b on the interior side of the slider 64, the collection assembly 35, and the collection carrier 18 with the collection absorbent 19 attached thereon and showing handle slots 25 and 26 of the collection assembly 35 for attaching the collection assembly 35 to the handle cover 28. FIG. 19 further shows the handle cover 28 with holding ridges 53 present in a specimen collector 50 of this embodiment. FIG. 20 shows a front view of a cassette 10 having a clean punch area 40 and having a support cap void 31 mateable with a support cap 24 of a collection assembly 35, and access void 17. FIG. 21 shows a back view of cassette 10 having a collection assembly 35 attached thereon, and showing a collection absorbent 19 attached onto the collection assembly 35. The support cap 24 of collection assembly 35 is visible wedged in the void 31 of the cassette 10. A clean punch area 40 is also visible. FIG. 22 shows a front view of cassette 10 having a collection assembly 35 attached thereon, and showing a collection absorbent 19 attached onto the collection assembly 35, and a clean punch area 40.

The biological sample or evidence collection device described herein may include a protect apparatus to protect the specimen collector 50 with the attached cassette 10. A suitable protect apparatus may be as described in U.S. application Ser. No. 14/662,713, the disclosure of which is incorporated herein in its entirety.

The biological sample or evidence collection device described herein includes identification indicia. Suitable identification indicia includes any such indicia that associates the collected biological sample or evidence with a unique identification so that the collected biological sample or evidence may be tracked and accounted for. Examples of identification indicia include bar codes, identification numbers, thumbprints, fingerprints, numbers, letters, combinations of numbers and letters, and combinations thereof. The identification indicia may be included on multiple components of the evidence collection device. For instance, the same identification indicia may be on the sample collection carrier 18 and the cassette 10. Also, the identification indicia may be unique from other identification indicia fixed to the device. For instance, the components of the device (sample collection carrier, cassette, and handle) may each have the same bar code affixed thereon during manufacturing or packaging, and an additional identification indicia may be affixed by the analysis lab upon receipt. The devices described herein provide ample surface area to which multiple identification indicia may be affixed thereon. The identification indicia may be encoded in a bar code, magnetic strip, radio frequency identification tag (RFID), USB means, or other means known in the art for carrying identification information. The identification indicia or information may be associated to an identification form.

The biological sample or evidence collection device described herein may be provided with an identification card. Suitable identification cards will associate the device with the identification card by way of identical identification indicia. The identification card provides a user with a means to record important identification information that is associated with the device. The device described herein may be used with or without the identification card.

Definitions

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein the terms "biological sample" and "biological specimen" are used in their broadest sense and include liquid or non-liquid samples from a wide variety of sources. Representative types of biological samples include tissue scrapings, whole blood, urine, cervical secretions, bronchial aspirates, sputum, saliva, feces, serum, synovial and cerebrospinal fluid, as well as laboratory preparations such as purified or partially purified macromolecules and cell culture materials. By way of example, the biological sample may be body fluid, body excretion, a population of cells, saliva, urine, mucus, tissue, or other biological sample type known in the art. Further examples of biological samples include, physiological/pathological body liquids (e.g., secretions, excretions, exudates and transudates) or cell suspensions (e.g., blood, lymph, synovial fluid, semen, saliva containing buccal cells, skin scrapings, hair root cells, etc.) of humans and animals; physiological/pathological liquids or cell suspensions of plants; liquid products, extracts or suspensions of bacteria, fungi, plasmids, viruses etc.; liquid products, extracts or suspensions of parasites including helminths, protozoas, spirochetes, etc.; liquid extracts or homogenates of human or animal body tissues (e.g., bone, liver, kidney, etc.); media from DNA or RNA synthesis; mixtures of chemically or biochemically synthesized DNA or RNA; and any other source in which DNA and/or RNA is or can be in a liquid medium. Preferably, the liquid containing the biological samples evaporates after applying the biological sample to the dry solid medium leaving macromolecules in dry form prior to subsequent analysis.

The term "inert" is defined as molecules which have no deleterious interaction with macromolecules of interest within a sample and will not interfere with any subsequent analysis of the macromolecules.

The terms "storing", "storage", "stored" and other derivatives of "store", when referring to macromolecules including genetic material in dry form entrained to the collection absorbent, means the preservation of macromolecules in a form suitable for subsequent analysis and which has not undergone substantial degradation. The time period for which macromolecules, including genetic material, may be stored may be as short as the time necessary to transport a sample from the place of collection of the sample to the place where subsequent analysis is to be performed. The conditions under which the sample of macromolecules may be stored on the collection absorbent vary. Typically, samples are stored at temperatures from −200° C. to 40° C. In addition, stored samples may optionally be stored in dry or desiccated conditions or under an inert atmosphere. Storage may be for a few seconds up to many years, preferably, about 4 seconds up to 100 years or more.

The term "sorb" means that the composition of the invention is absorbed, or otherwise incorporated into or onto the solid matrix in such a way as not to be readily removed from the matrix unless subjected to conditions which are intentionally or inadvertently performed to remove the sorbed composition from the solid matrix.

The term "weak base" includes a composition which has a pH of about 6 to 10, preferably about pH 8 to 9.5. One function of the weak base is to act as a buffer to maintain a composition pH of about 6 to 10, preferably about pH 8.0 to 9.5, for example, pH 8.6.

EXAMPLES

The following examples are simply intended to further illustrate and explain the present invention. The invention, therefore, should not be limited to any of the details in these examples.

Example 1

Collection of Evidence at a Crime Scene

The user of the collection device will retrieve the collection components from sterile primary packaging of the device. The sample collector and the cassette of the sample collection device may come packaged together, or they may be packaged separately. The specimen collector 50 may have the specimen collection assembly 35 and the slider 64 pre-attached to the handle cover 28. Alternatively, the user may attach the handle cover 28 to the specimen collection assembly 35, and attach the slider 64 to the handle cover 28. Any protective film or packaging covering the collection absorbent may be removed using sterile techniques (e.g., wearing sterile gloves, handling with sterile precautions, etc.). The user may then slide the slider 64 down to expose the collection absorbent 19, and contact the collection absorbent 19 to surfaces having potential evidence or biological samples for collection. If the user desires to collect a biological sample from an unwilling suspect, attaching the handle 28 and the slider 64 will aid in collecting the sample without endangering the appendages of the user, and the whole thing will provide all the support, stiffness, protection, etc.

The user may apply additives to the collected specimen on the collection absorbent 19 to preserve the biological sample or evidence, or inactivate potential pathogens. The user may apply preservative additives to the collected specimen on the collection absorbent 19 through holes 99 of the handle cover 28, directly onto the collection absorbent 19 when the slider 64 is moved backwardly, or through holes 73 of the slider 64 when the slider is moved forwardly. The ventilation holes 99 of the handle cover 28, the ventilation holes 73 of the slider 64, and the ventilation gap created by the engagement of the protrusion 72 of the slider 64 with the elevated support cap 24 of the collection assembly 35 significantly accelerate drying of the collected specimen or the combination of collected specimen and preservative additives to prevent deterioration of the collected specimen.

Once the biological sample or evidence has been collected, the user may allow the collected specimen to dry.

The user may then attach the specimen collection assembly 35 to the cassette 10 by aligning the sample collection carrier 18 of the specimen collection assembly 35 between the first collector retaining flange 15 and the second collector retaining flange 16 and sliding the sample collection carrier 18 within the flanges 15 and 16 until the bottom end of the collection carrier 18 engages the back stop 95, such that the collection absorbent 19 aligns with the receiver impression 14 and over the access void 17. The first cassette attachment void 20 and the second cassette attachment void 21 of the sample collection carrier 18 should align with the first collector attachment peg 12 and the second collector attachment peg 13 of the cassette 10. Additionally, the top end of the elevated cap 24 should engage the front stop 38. In embodiments where the cassette 10 further comprises a support cap void 55, the elevated cap 24 should engage the support cap void 55, thereby further securing the sample collection carrier 18 to the cassette 10. The flanges 15 and 16, the back stop 95, the front stop 38, and the support cap void 55 (if present) collaborate to retain and secure the specimen collection assembly 35 in alignment in the cassette 10 such that the collection absorbent 19 aligns with the receiver impression 14 and over the access void 17. The user then may further attach the sample collection carrier 18 to the cassette 10 by pressing the pegs (12 and 13), if present, into the attachment voids (20 and 21). The user may attach the pegs 12 and 13 into the attachment voids 20 and 21 by pressing on the sides of the specimen collection assembly 35. Alternatively, and preferably, the user may attach the pegs 12 and 13 into the attachment voids 20 and 21 by pressing on the slider head 66 of the slider 64, thereby indirectly pressing on the sides of the specimen collection assembly 35. In embodiments where the slider head 66 of the slider 64 further comprises protrusions 54*a* and *b* on the interior side of the slider head 66, protrusions 54*a* and *b*, which are in register with the collector attachment voids 20 and 21, facilitate the function of the slider head 66 in attaching the pegs 12 and 13 into the attachment voids 20 and 21 by providing pressure points for pushing and securing the pegs 12 and 13 into the attachment voids 20 and 21.

After attaching the specimen collection assembly 35 to the cassette 10, the specimen collection assembly 35 comprising the biological sample or evidence may be stored or transported with the handle cover 28 attached thereon. The handle cover 28 may further be detached from the specimen collection assembly 35, thereby transferring the specimen collection assembly 35 from the handle cover 28 to the cassette 10, and providing a cassette 10 having a specimen collection assembly 35 attached thereon for storage and subsequent downstream manipulation, the specimen collection assembly 35 comprising the biological sample or evidence. The handle cover 28 is detached from the specimen collection assembly 35 by guiding the carrier attachment pegs, such as pegs 29 and 30 on the handle cover 28, out of the entry point of the handle slot. Detaching the handle cover 28 from the specimen collection assembly 35 may be facilitated by a plurality of impressions, such as a first impression 56 and a second impression 57, which provide access for a plurality of carrier attachment pegs on the handle 28, such as a first carrier attachment peg 29 and a second carrier attachment peg 30, after the specimen collection assembly 35 is attached to the cassette 10.

The user may complete an identification form or identification card that includes an identification indicia on the form identical to identification indicia located on the cassette 10. The identical identification indicia may also be located on the sample collection carrier 18. The identification form and the collection device may then be submitted for further analysis at a laboratory.

Components of the collection device and the information form may include areas where additional identification indicia may be added for identification means in the laboratory. Once the collection device is received by the analysis laboratory, the identification information associated with the cassette 10 may be entered into a database or computer system. The means of entering such information depends upon the identification indicia storage means. For instance, if the identification indicia is a bar code, the cassette may be scanned. If the identification indicia is a magnetic strip, the cassette may be swiped in a device that can read magnetic strip encoding.

The cassette comprising the specimen collected on the specimen collection absorbent 19 may be placed in a sample tray of an automated device or machine that punches samples from the collection absorbent 19. Typically, the punches will be collected in a vial. The vial or a plate containing the vial will be transferred to an automated sequencing machine and analyzed. The identification information is associated with the sample by the automated analysis devices such that the resultant readout information is associated with the correct identification information.

The invention illustratively disclosed herein suitably may be practiced in the absence of any element, which is not specifically disclosed herein. It is apparent to those skilled in the art, however, that many changes, variations, modifications, other uses, and applications to the method are possible, and also changes, variations, modifications, other uses, and applications which do not depart from the spirit and scope of the disclosure are deemed to be covered by the disclosure, which is limited only by the claims which follow.

What is claimed is:

1. A specimen collection device comprising:
   a. a specimen collection assembly comprising a sample collection carrier and a collection absorbent connected to the specimen collection carrier through a raised cap;
   b. a handle cover comprising an attachment means for removably connecting the handle to the specimen collection assembly and further comprising ventilation holes which provide for the drying of and the addition of additives to a collected specimen;
   c. a sliding cover removably and slidably connected to the handle cover, the sliding cover having an elongated body and a head connected to the body on one end of the body and a protrusion that engages the raised cap when the sliding cover is moved forwardly on the handle cover, and wherein the sliding cover further comprises ventilation holes which provide for the drying of and the addition of additives to a collected specimen; and d. a specimen collector cassette into which the specimen collected is secured, the cassette having a registration track configured to register with the shape of the specimen collection assembly upon insertion of the specimen collection assembly into the registration track, wherein the specimen collector cassette comprises a void in unobstructed registration with the collection absorbent when the specimen collector assembly is attached to the specimen collector cassette thereby providing unobstructed access to a collected specimen for automated analysis.

2. The device of claim 1, wherein the specimen collection assembly further comprises a cover and a means for attaching the cover to the specimen collection cassette, wherein the cover permits a user to press the cover into contact with the collection absorbent without the user directly contacting the collection absorbent.

3. The device of claim 1, wherein the specimen collection cassette further comprises identification indicia.

4. The device of claim 1, wherein the specimen collector cassette further comprises a clean punch area.

5. The specimen collection device of claim 1, wherein the sliding cover of c. does not surround the collection absorbent.

6. A specimen collection device comprising:
a. a specimen collection assembly comprising a sample collection carrier and a collection absorbent connected to the specimen collection carrier through a raised cap;
b. a handle cover comprising an attachment means for removably connecting the handle to the specimen collection assembly, wherein the handle cover comprises ventilation holes which provide for the drying or the addition of additives to a collected specimen;
c. a sliding cover removably and slidably connected to the handle cover, the sliding cover having a protrusion that engages the raised cap when the sliding cover is moved forwardly on the handle cover, wherein the sliding cover further comprises ventilation holes which provide for the drying of and the addition of additives to a collected specimen; and
d. a specimen collector cassette into which the specimen collected is secured, the cassette having a clean punch area and a registration track configured to register with the shape of the specimen collection assembly upon insertion of the specimen collection assembly into the registration track, wherein the specimen collector cassette comprises a void in unobstructed registration with the collection absorbent when the specimen collector assembly is attached to the specimen collector cassette thereby providing unobstructed access to a collected specimen for automated analysis.

7. The device of claim 6, wherein the specimen collection assembly further comprises a cover and a means for attaching the cover to the specimen collection cassette, wherein the cover permits a user to press the cover into contact with the collection absorbent without the user directly contacting the collection absorbent.

8. The device of claim 6, wherein the specimen collection cassette further comprises identification indicia.

9. The specimen collection device of claim 6, wherein the sliding cover of c. does not surround the collection absorbent.

10. A method of supporting a biological sample collection absorbent to provide for collecting a biological specimen, efficiently drying the collected specimen, using the original absorbent in an automated analytical system, and allowing for storage of the biological sample collection absorbent, the method comprising:
a. providing a specimen collection assembly comprising a sample collection carrier and a collection absorbent connected to the specimen collection carrier through a raised cap;
b. providing a handle cover comprising an attachment means for removably connecting the handle to the specimen collection assembly, wherein the handle cover permits manipulation of the specimen collection assembly during specimen collection when the handle cover is attached to the specimen collection assembly, and wherein the handle cover comprises ventilation holes which provide for the drying of and the addition of additives to a collected specimen;
c. providing a sliding cover removably and slidably connected to the handle cover, the sliding cover having an elongated body and a head connected to the body on one end of the body and a protrusion that engages the raised cap when the sliding cover is moved forwardly on the handle cover thereby raising the head of the sliding cover above the collection absorbent and creating a ventilation gap between the head of the sliding cover and the collection absorbent, and wherein the head further comprises ventilation holes which provide for the drying of and the addition of additives to a collected specimen;
d. connecting the sample collection assembly and the sliding cover to the handle cover to produce a sample collector;
e. sliding the sliding cover backwardly to expose the sample collection absorbent;
f. collecting a biological sample, wherein the biological sample is contacted with the collection absorbent;
g. sliding the sliding cover forwardly to cover the sample collection absorbent thereby creating a ventilation gap between the handle cover and the collection absorbent;
h. drying the collected sample;
i. removing the sliding cover from the handle cover;
j. connecting the sample carrier to a cassette;
k. removing the handle cover from the sample collection carrier; and, l. storing the collection cassette.

11. The method of claim 10, further comprising applying a preservative additive to the collection absorbent after collecting the biological sample.

12. The method of claim 10, further comprising inserting the collection cassette into an automatic sampling device.

13. The method of claim 10, wherein the sliding cover of c. does not surround the collection absorbent.

* * * * *